US012710364B2

(12) United States Patent
Kouda

(10) Patent No.: US 12,710,364 B2
(45) Date of Patent: Aug. 18, 2026

(54) ASSESSMENT OF CLEANING PROCEDURES OF A BIOTHERAPEUTIC MANUFACTURING PROCESS

(71) Applicant: AMGEN INC., Thousand Oaks, CA (US)

(72) Inventor: Rammahipal Kouda, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 735 days.

(21) Appl. No.: 17/928,671

(22) PCT Filed: Jun. 3, 2021

(86) PCT No.: PCT/US2021/035739
§ 371 (c)(1),
(2) Date: Nov. 30, 2022

(87) PCT Pub. No.: WO2021/247892
PCT Pub. Date: Dec. 9, 2021

(65) Prior Publication Data

US 2023/0273126 A1 Aug. 31, 2023

Related U.S. Application Data

(60) Provisional application No. 63/089,329, filed on Oct. 8, 2020, provisional application No. 63/034,874, filed on Jun. 4, 2020.

(51) Int. Cl.
*G01N 21/552* (2014.01)
*G01N 21/94* (2006.01)
(Continued)

(52) U.S. Cl.
CPC .......... *G01N 21/554* (2013.01); *G01N 21/94* (2013.01); *G01N 30/02* (2013.01); *G01N 33/54366* (2013.01); *G01N 2030/027* (2013.01)

(58) Field of Classification Search
CPC .......... G01N 2030/027; G01N 21/553; G01N 21/554; G01N 21/94; G01N 30/02; G01N 33/54366; G01N 33/54373
(Continued)

(56) References Cited

U.S. PATENT DOCUMENTS 6,143,874 A 11/2000 Chang
6,184,359 B1 2/2001 Grabstein et al.
(Continued)

FOREIGN PATENT DOCUMENTS

WO 2018/204907 A1 11/2018
WO 2019/140196 A1 7/2019

OTHER PUBLICATIONS

Boozer et al., "Looking towards label-free biomolecular interaction analysis in a high-throughput format: a review of new surface plasmon resonance technologies," *Current Opin Biotech* 17:400-405 (2006).

(Continued)

*Primary Examiner* — Sunghee Y Gray
(74) *Attorney, Agent, or Firm* — Julie J. Hong

(57) ABSTRACT

Provided herein are methods of assessing or validating a cleaning procedure of a biotherapeutic manufacturing process, said method comprising analyzing by a surface plasmon resonance (SPR)-based assay the binding activity of a cleaned sample to a ligand which binds to a biotherapeutic produced by the manufacturing process. In various embodiments, the cleaning procedure comprises one or more steps to inactivate and/or degrade the biotherapeutic. In various
(Continued)

instances, the method demonstrates that greater than about 99.99% degradation of the therapeutic is achieved by the cleaning procedure comprising the one or more steps to inactivate and/or degrade the biotherapeutic.

25 Claims, 4 Drawing Sheets

(51) Int. Cl.
*G01N 30/02* (2006.01)
*G01N 33/543* (2006.01)

(58) Field of Classification Search
USPC .......................................................... 356/445
See application file for complete search history.

(56) References Cited

U.S. PATENT DOCUMENTS 6,232,447 B1 5/2001 Cerretti
6,235,883 B1 5/2001 Jakobovits et al.
6,319,499 B1 11/2001 Elliott
6,355,779 B1 3/2002 Goodwin et al.
6,500,429 B2 12/2002 Boone et al.
6,596,852 B2 7/2003 Cerretti et al.
6,630,143 B1 10/2003 Lyman et al.
6,682,736 B1 1/2004 Hanson et al.
6,692,740 B2 2/2004 Sims et al.
6,716,587 B2 4/2004 Mosley et al.
6,740,522 B2 5/2004 Anderson
6,849,450 B2 2/2005 Langley et al.
6,924,360 B2 8/2005 Green et al.
7,037,498 B2 5/2006 Cohen et al.
7,045,128 B2 5/2006 Lyman et al.
7,067,131 B2 6/2006 Gudas et al.
7,081,523 B2 7/2006 Elliott
7,084,257 B2 8/2006 Deshpande et al.
7,090,844 B2 8/2006 Bar-Eli et al.
7,109,003 B2 9/2006 Hanson et al.
7,132,281 B2 11/2006 Hanson et al.
7,135,174 B2 11/2006 Corvalan et al.
7,138,500 B1 11/2006 Goodwin et al.
7,141,653 B2 11/2006 Greenfeder et al.
7,144,731 B2 12/2006 Zsebo
7,186,809 B2 3/2007 Pluenneke
7,193,058 B2 3/2007 Cosman et al.
7,199,224 B2 4/2007 Black et al.
7,202,343 B2 4/2007 Gudas et al.
7,265,212 B2 9/2007 Babcook et al.
7,267,960 B2 9/2007 Galibert et al.
7,270,817 B2 9/2007 Sims et al.
7,285,269 B2 10/2007 Babcook et al.
7,288,251 B2 10/2007 Bedian
7,288,253 B2 10/2007 Roskos et al.
7,304,144 B2 12/2007 Sims et al.
7,317,090 B2 1/2008 Mosley et al.
7,318,925 B2 1/2008 Roskos et al.
7,326,414 B2 2/2008 Bedian et al.
7,335,743 B2 2/2008 Welcher et al.
7,338,660 B2 3/2008 Bedian et al.
7,371,381 B2 5/2008 Aaron et al.
7,378,091 B2 5/2008 Gudas et al.
7,411,050 B2 8/2008 Anderson
7,411,057 B2 8/2008 Hanson et al.
7,422,742 B2 9/2008 Greenfeder et al.
7,423,128 B2 9/2008 Gazit-Bornstein et al.
7,427,669 B2 9/2008 Cosman et al.
7,435,796 B1 10/2008 Yoshinaga
7,438,910 B2 10/2008 Varnum et al.
7,449,555 B2 11/2008 Fanslow et al.
7,465,450 B2 12/2008 Pluenneke
7,498,420 B2 3/2009 Michaud et al.
7,521,048 B2 4/2009 Gliniak et al.
7,521,053 B2 4/2009 Oliner
7,537,762 B2 5/2009 North et al.
7,541,438 B2 6/2009 Tamatani et al.
7,563,442 B2 7/2009 Bedian et al.
7,566,772 B2 7/2009 Green et al.
7,569,387 B2 8/2009 Theill et al.
7,579,186 B1 8/2009 Sakamoto et al.
7,585,500 B2 9/2009 Foltz et al.
7,592,429 B2 9/2009 Paszty et al.
7,592,430 B2 9/2009 Bedian et al.
7,601,818 B2 10/2009 Wild, Jr. et al.
7,618,633 B2 11/2009 Bedian et al.
7,626,012 B2 12/2009 Bedian et al.
7,628,986 B2 12/2009 Weber et al.
7,638,606 B2 12/2009 Carter et al.
7,658,924 B2 2/2010 Oliner et al.
7,695,948 B2 4/2010 Black et al.
7,700,742 B2 4/2010 Cohen et al.
7,704,501 B2 4/2010 Anderson
7,705,130 B2 4/2010 Rothe et al.
7,709,611 B2 5/2010 Li et al.
7,718,776 B2 5/2010 Boyle et al.
7,728,110 B2 6/2010 Babcook et al.
7,728,113 B2 6/2010 Bedian et al.
7,736,644 B2 6/2010 Weber et al.
7,741,115 B2 6/2010 Baum et al.
7,767,206 B2 8/2010 Tocker et al.
7,767,793 B2 8/2010 Sims
7,786,271 B2 8/2010 Sims et al.
7,786,284 B2 8/2010 Tocker et al.
7,790,859 B2 9/2010 Welcher et al.
7,795,413 B2 9/2010 Wild, Jr. et al.
7,807,159 B2 10/2010 Chin et al.
7,807,795 B2 10/2010 Boyle
7,807,796 B2 10/2010 Cosman et al.
7,807,797 B2 10/2010 Hanson et al.
7,807,798 B2 10/2010 Jakobovits et al.
7,815,907 B2 10/2010 Cohen et al.
7,824,679 B2 11/2010 Hanson et al.
7,833,527 B2 11/2010 Tocker et al.
7,867,494 B2 1/2011 Liu et al.
7,868,140 B2 1/2011 Siu et al.
7,871,611 B2 1/2011 Calzone et al.
7,872,106 B2 1/2011 Paszty et al.
7,872,113 B2 1/2011 Carter et al.
7,879,323 B2 2/2011 Thomason et al.
7,887,799 B2 2/2011 Thomason et al.
7,888,482 B2 2/2011 Virca et al.
7,906,625 B2 3/2011 Shen et al.
7,915,391 B2 3/2011 Ng et al.
7,923,008 B2 4/2011 Boyle
7,932,372 B2 4/2011 Pullen et al.
7,939,070 B2 5/2011 Tocker et al.
7,939,640 B2 5/2011 Baum
7,947,809 B2 5/2011 Yan et al.
7,964,193 B2 6/2011 Green et al.
8,945,860 B2 2/2015 Yang et al.
2003/0103978 A1 6/2003 Deshpande et al.
2006/0127393 A1 6/2006 Li et al.
2007/0196376 A1 8/2007 Raeber et al.
2008/0166352 A1 7/2008 Siu et al.
2008/0182976 A1 7/2008 Elliott
2008/0286284 A1 11/2008 Maddon et al.
2008/0292639 A1 11/2008 Shen et al.
2009/0041784 A1 2/2009 Yan et al.
2009/0155164 A1 6/2009 Brasel et al.
2009/0155274 A1 6/2009 Wild, Jr. et al.
2009/0191212 A1 7/2009 Oliner et al.
2009/0208489 A1 8/2009 Veiby et al.
2009/0214559 A1 8/2009 Varnum et al.
2009/0226447 A1 9/2009 Boone et al.
2009/0234106 A1 9/2009 Han et al.
2009/0238823 A1 9/2009 Comeau et al.
2009/0263383 A1 10/2009 Smothers et al.
2010/0040619 A1 2/2010 Li et al.
2010/0047253 A1 2/2010 Foltz et al.
2010/0098694 A1 4/2010 Bedian et al.
2010/0111979 A1 5/2010 Weber et al.
2010/0197005 A1 8/2010 Belouski et al.
2010/0209435 A1 8/2010 Boyle et al.
2010/0254975 A1 10/2010 Hsu et al.

(56) References Cited

U.S. PATENT DOCUMENTS

| | | | | |
|---|---|---|---|---|
| 2010/0255538 | A1 | 10/2010 | Cohen et al. | |
| 2010/0305307 | A1 | 12/2010 | Jakobovits et al. | |
| 2010/0311119 | A1* | 12/2010 | Hermans | C07K 16/4283 435/254.2 |
| 2011/0014201 | A1 | 1/2011 | Smith et al. | |
| 2011/0027287 | A1 | 2/2011 | Jackson et al. | |
| 2011/0040076 | A1 | 2/2011 | Wild, Jr. et al. | |
| 2011/0044986 | A1 | 2/2011 | Biere-Citron et al. | |
| 2011/0045537 | A1 | 2/2011 | Welcher et al. | |
| 2011/0059063 | A1 | 3/2011 | Virca et al. | |
| 2011/0091455 | A1 | 4/2011 | Chin et al. | |
| 2011/0135657 | A1 | 6/2011 | Hu et al. | |
| 2011/0150888 | A1 | 6/2011 | Bakaletz et al. | |
| 2011/0165171 | A1 | 7/2011 | Virca et al. | |
| 2016/0103066 | A1* | 4/2016 | Schasfoort | G01N 21/553 436/171 |
| 2019/0071513 | A1* | 3/2019 | Hernandez-Hoyos | A61P 35/02 |

OTHER PUBLICATIONS

Chothia et al., "Confirmations of Immunoglobulin Hypervariable Regions," *Nature* 342:877-883 (1989).

Chothia and Lesk et al., "Canonical Structures for the Hypervariable Regions of Immunoglobulins," *J. Mol. Biol*. 196(4):901-917 (1987).

Daniel et al., "The denaturation and degradation of stabel enzymes at high temperatures," *Biochem. J.* 317(1):1-11 (1996).

Frenzel et al., "Expression of recombinant antibodies," *Front. Immunol*. 4:217 (2013).

Grönberg and Hjorth (2018), 'Cleaning-in-Place and Sanitization' eds. Jagschies et al., *Biopharmaceutical Processing: Development, Design, and Implementation of Manufacturing Process*, Amsterdam, Netherlands, Elsevier, 675-699.

Guo, "Surface plasmon resonance based biosensor technique: A review," *J. Biophotonics* 5(7):483-501 (2012).

Sharnez et al., "Biopharmaceutical Cleaning Validation: Acceptance Limits for Inactivated Product Based on Gelatin as a Reference Impurity," *Journal of Validation Technology* 18(4):42-45 (2013).

Shimamoto et al., "Peptibodies: A flexible alternative format to antibodies," *mAbs* 4(5):586-591 (2012).

Spiess et al., "Alternative molecular formats and therapeutic applications for bispecific antibodies," *Mol Immunol*. 67 (2 Pt. A):95-106 (2015).

Thillaivinayagalingam et al., "Biopharmaceutical production: Applications of surface plasmon resonance biosensors," *Journal of Chromatography B* 878(2):149-153 (2010).

Whitaker et al., "Chemical and physical modification of proteins by the hydroxide ion," *Critical Reviews in Food Science and Nutrition* 19(3):173-212 (1983).

Kaminagayoshi et al., "Study on an Inactivation Evaluation Method of Cleaning Processes for Biopharmaceuticals," *BioPharm International*, pp. 22-28, Sep. 2018.

Kouda et al., "Degradation of Biopharmaceuticals During Cleaning Processes: Comparing Two Different Analytical Methods for Assessment with Bispecific Antibodies," *BioProcess International* 21(6):1-10 (2023).

* cited by examiner

FIGURE 1A

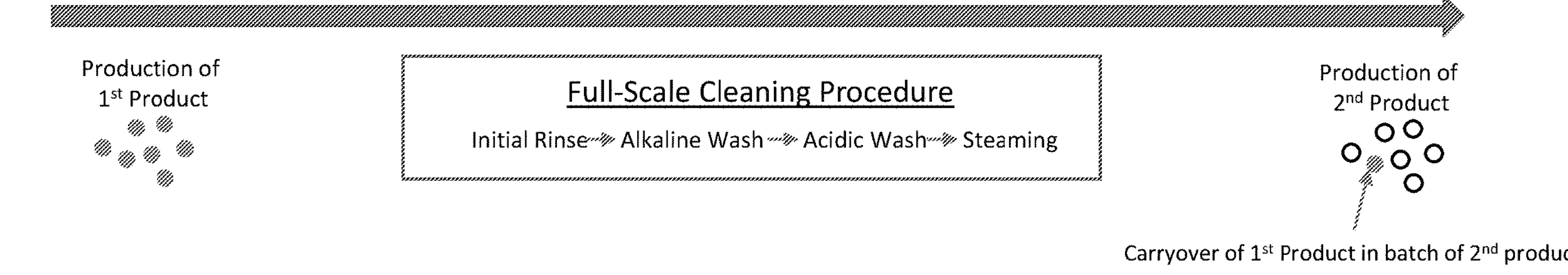

FIGURE 1B

*Cleaning Validation of Full-Scale Cleaning Procedure*

*"Is the carryover of the 1st Product acceptable from a safety standpoint?"*

Small-Scale Cleaning Procedure*

Alkaline Wash → Acidic Wash → Steaming

* Simulating full-scale cleaning procedure or worst-case full-scale cleaning procedure.

| Biotherapeutic Product | ADE of Inactivated Product (µg) | ADE of Active Product (µg) | % Degradation[1] |
|---|---|---|---|
| **mAbs** | 650 | 10-100 | 98-85% |
| **Peptibodies** | | 1-10 | 99.8-98.5% |
| **High Potent** | | 0.1-1 | 99.98-99.85-% |
| **Very High Potent** | | **0.001** | **>99.99%** |

As Biotherapeutic Potency increases → ADE of Active Biotherapeutic Decreases; % Degradation of Active Biotherapeutic Increases

***For a very high potent biotherapeutic, one must demonstrate that >99.99% degradation has been achieved.

[1] % Degradation is calculated using formula: $\% \text{ Degradation} = 1 - \frac{ADE\ of\ Active\ Product}{650 \mu g}\%$ Plasmon Wave
Reflected Light
Absorbed Light
Flow Cell
Reflection
Absorbance
Reflection
Detector
Surface Plasmon
Resonance
Angle
Angle of
Reflection
Single Wavelength
Multi Angle Light
Light Source
Single Wavelength
Fixed Angle Light
Prism
Metal Surface
Dextran
Conjugated
Ligand

Figure 3A

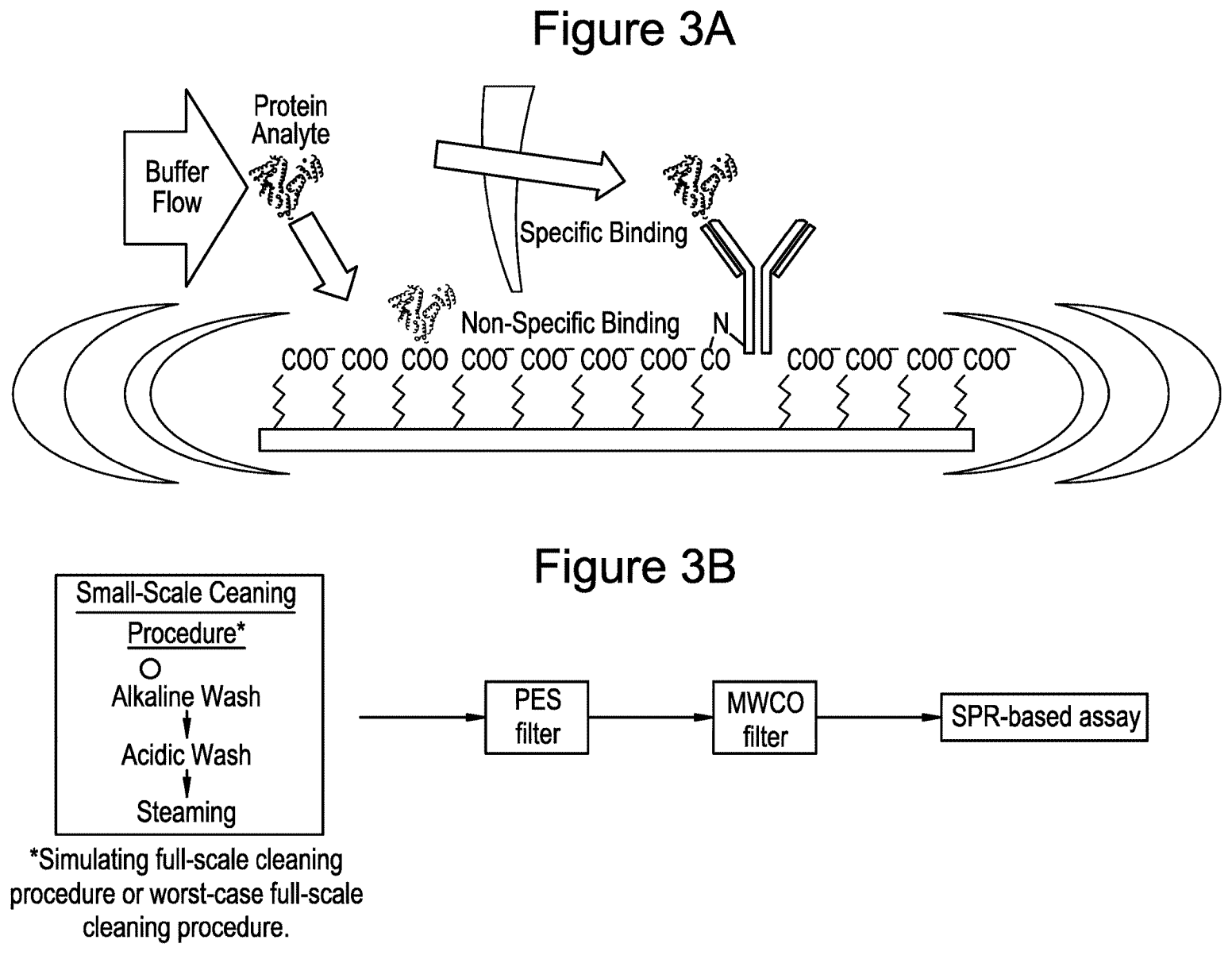

Buffer Flow
Protein Analyte
Specific Binding
Non-Specific Binding
N
COO⁻ COO COO COO⁻ COO⁻ COO⁻ COO⁻ CO COO⁻ COO⁻ COO⁻ COO⁻

Figure 3B

Small-Scale Ceaning Procedure*
○
Alkaline Wash
Acidic Wash
Steaming
*Simulating full-scale cleaning procedure or worst-case full-scale cleaning procedure.
PES filter
MWCO filter
SPR-based assay

ASSESSMENT OF CLEANING PROCEDURES OF A BIOTHERAPEUTIC MANUFACTURING PROCESS

CROSS-REFERENCE TO RELATED APPLICATIONS

This application is a national stage application of International Application No. PCT/US2021/035739, filed on Jun. 3, 2021, which claims the benefit under 35 U.S.C. § 119 (e) of U.S. Provisional Patent Application No. 63/034,874, filed on Jun. 4, 2020, and U.S. Provisional Patent Application No. 63/089,329, filed on Oct. 8, 2020. The disclosure of each aforementioned application is incorporated by reference herein.

BACKGROUND

To guarantee product safety, efficient cleaning, sanitization, and sterilization procedures are required aspects of a biotherapeutic manufacturing process. Cleaning is the procedure by which impurities (both product-related and process-related) and contaminants are removed to minimize carryover to the next cycle of a process. Cleaning also is a means by which the life length of filters and resins is increased. Because cleaning occurs without disassembling the equipment of the manufacturing process, it is often referred to as "cleaning-in-place" or "CIP". Sanitization is a procedure by which biological agents (e.g., viruses, bacteria, and spores) are reduced to a pre-determined level, and sterilization is a procedure by which living microorganisms including spores are eliminated. See, e.g., Gronberg and Hjorth (2018), 'Cleaning-in-Place and Sanitization' eds. Jagschies et al., *Biopharmaceutical Processing: Development, Design, and Implementation of Manufacturing Process*, Amsterdam, Netherlands, Elsevier, 676.

Some manufacturing facilities are set up to produce different biotherapeutics in series using the same process equipment. Such multiproduct manufacturing processes are advantageous, given the reduction in cost and required resources (e.g., physical space, human operators), compared to manufacturing processes comprising multiple single-product processes. The cleaning, sanitization and sterilization procedures used in such multiproduct manufacturing processes are very important. Regulatory bodies, like the U.S. Food and Drug Administration (FDA) and the European Medicines Agency (EMA), emphasize, not only the sufficiency of the cleaning, sanitization, and sterilization procedures themselves, but also the validation techniques of these procedures (Gronberg and Hjorth (2018), supra).

Total Organic Carbon (TOC) assays, silver staining of SDS-PAGE gels, and total protein assays are among the assays frequently used for cleaning validation (Gronberg and Hjorth (2018), supra). An effective multiproduct cleaning validation will demonstrate that the carryover of a first manufactured product in a batch of the second manufactured product is acceptable from a predictive safety standpoint. The maximum allowable carryover (MAC) describes the upper limit of the carryover of the first product in a batch of the second manufactured product. If the carryover is above the MAC, then the cleaning procedure is deemed insufficient. In exemplary embodiments, the MAC is based on the ADE (acceptable daily exposure) of the first product as well as the mass of the second manufactured product in a batch and the mass of the second manufactured product of a daily dose. In various aspects, MAC is the ADE of the first product*(mass of the second manufactured product in a batch/mass of the second manufactured product in a daily dose).

As the potency of the first product of a multiproduct manufacturing process increases, the ADE for the first product decreases. For example, for high potent biotherapeutic products, the ADE is about 0.1 μg to about 1.0 μg, and, for products of very high potency, the ADE is 0.001 μg. Consequently, the cleaning requirements (e.g., stringency of cleaning conditions, types and numbers of cleaning agents) increase, and the sensitivity of the analytical method used in cleaning validation likewise increases, given that the analytical method must detect significantly low amounts (e.g., less than 1 μg) of the first product. Many techniques and assays currently used for cleaning validation are not sensitive enough to detect and quantify the low amounts of product carryover.

Some cleaning procedures of biotherapeutic manufacturing processes comprise exposing the process equipment to extreme pH (e.g., below 3, above 12) and/or high temperatures which will degrade and/or inactivate the first product (Whitaker et al., Crit Rev Food Sci Nutr 19(3): 173 (1983); Daniel et al., Biochem J 317: 1 (1996)). In such cases, the acceptance limits for cleaning validation may be based on the inactivated product. The acceptance limits for inactivated products are discussed in Sharnez et al., *J. of Validation Technology, Vol* 18, No. 4, p 42-45, 2012, and the MAC is described therein as 650 μg of the inactivated/degraded product. For purposes of validating cleaning procedures comprising an inactivation and/or degradation, inactivation/degradation studies are carried out to demonstrate that the appropriate extent of inactivation/degradation was achieved, and that the amount of inactivated and/or degraded product does not exceed the MAC (650 μg).

Bench-scale inactivation/degradation studies are performed to assess the cleaning process and determine the extent of product degradation. To calculate the required degradation of the first product, the following equation is used:

$$\%\ \text{Degradation} = 1 - \frac{(ADE\ \text{of Active Product})}{650\ \mu g} * 100\%$$

For monoclonal antibodies, the ADE for the active form (e.g., neither inactivated nor degraded) is about 10 μg to about 100 μg and the required % degradation according to the above formula is about 85% to about 98%. For peptibodies, the ADE is about 1 μg to about 10 μg and the required % degradation according to the above formula is about 98.5% to about 99.8%. For biotherapeutics having high potency, the ADE is about 0.1 μg to about 1 μg and the required % degradation according to the above formula is about 99.85% to about 99.98%. For biotherapeutics having very high potency, the ADE is about 0.001 μg and the required % degradation according to the above formula is >99.99%. Accordingly, for validating cleaning procedures of a multiproduct manufacturing process, wherein the first product is inactivated and/or degraded, it must be demonstrated that (1) the carryover of the first product (in its active form) into a batch of the subsequently manufactured product is less than the ADE and/or (2) the % degradation achieved by the cleaning procedure is about 85% to about 98% for monoclonal antibodies, about 98.5% to about 99.8% for peptibodies, about 99.85% to about 99.98% for higher potency molecules, and greater than 99.99% for very high potency biotherapeutics. Given that the average potency for some biotherapeutics is in the range of about 0.001 μg to about 1 μg, there is a need in the art for cleaning validation assays that can detect low amounts of active biotherapeutic, e.g., less than 1 μg) and able to demonstrate that a very high level of degradation (>99.99%) of the active biotherapeutic was achieved by the cleaning procedure.

SUMMARY

Presented herein for the first time are data demonstrating results from inactivation and/or degradation studies performed at bench-scale. Using a highly sensitive analytical method, it was shown that 99.999% of the Drug Substance/Drug Product (DS/DP) is degraded/inactivated when exposed to the cleaning cycles used at the manufacturing site. These data suggest that, for a highly potent molecule, bench scale inactivation-degradation methods followed by validation by the described analytical method, satisfies the requirement to demonstrate significant degradation.

The present disclosure provides cleaning validation assays for a biotherapeutic manufacturing process. In exemplary aspects, the biotherapeutic manufacturing process is a multiproduct manufacturing process. In exemplary embodiments, the cleaning validation assay comprises determining the binding activity of a cleaned sample to a ligand which binds to the biotherapeutic produced by the biotherapeutic manufacturing process. In various instances, the binding activity is determined by a surface plasmon resonance (SPR)-based assay, which correlates the binding activity to a concentration of the biotherapeutic. The cleaned sample is in various aspects obtained by carrying out a small-scale cleaning procedure, which simulates a large-scale cleaning procedure, on a sample comprising the biotherapeutic. The present disclosure provides methods of assessing or validating a cleaning procedure of a biotherapeutic manufacturing process. In exemplary embodiments, the method comprises analyzing the binding activity of a cleaned sample to a ligand which binds to a biotherapeutic produced during the manufacturing process. In exemplary embodiments, the method comprises (a) carrying out a small-scale cleaning procedure, which simulates a large-scale cleaning procedure, on a sample comprising the biotherapeutic produced by the biotherapeutic manufacturing process, to obtain a cleaned sample, and (b) determining the binding activity of the cleaned sample to a ligand which binds to the biotherapeutic, wherein the binding activity is determined by a surface plasmon resonance (SPR)-based assay. In various embodiments, the cleaning procedure comprises one or more steps to inactivate or degrade a biotherapeutic. In various instances, the cleaning procedure comprises at least one degradation step and/or at least one inactivation step purposed for degrading and/or inactivating the biotherapeutic. Suitable cleaning procedures, including cleaning procedures comprising an inactivation and/or degradation of the biotherapeutic, are known in the art. See, e.g., Gronberg and Hjorth (2018), supra). In exemplary aspects, the cleaning procedure comprises an alkaline wash, an acidic wash, a high temperature step, or any combination thereof. Optionally, prior to the cleaning procedure, there is a dirty hold time (DHT) carried out at ambient or high humidity conditions. In various aspects, the high temperature step comprises steaming, optionally, a steaming in place (SIP). In various instances, the high temperature step occurs at a temperature greater than 100 degrees C. In various instances, the high temperature step occurs at a temperature greater than 110 degrees C. or greater than 120 degrees C., optionally, in an autoclave. In various aspects, the alkaline wash and/or the acidic wash occur at a high temperature, optionally, a temperature greater than 100 degrees C. Alternatively, the alkaline wash and/or the acidic wash occur at an ambient temperature, optionally, a temperature of about 20 degrees C. to about 30 degrees C. Optionally, the alkaline wash and/or the acidic wash occurs with shaking. In various instances, the alkaline wash occurs at a pH of 11 or higher and/or the acidic wash occurs at a pH less than 3. The cleaning procedure comprises in exemplary instances a pH neutralization after the alkaline wash and/or the acidic wash. In exemplary aspects, the assay or method comprises determining the binding activity of a cleaned sample to a ligand which binds to the biotherapeutic produced by the biotherapeutic manufacturing process, wherein the binding activity is determined by a surface plasmon resonance (SPR)-based assay. In exemplary instances, the ligand is attached to a face of a solid support, and the assay or method optionally comprises contacting the face to which the ligand is attached with a solution comprising the cleaned sample. Optionally, the solid support comprises a metal surface and a dextran coating. In various instances, a single wavelength light is shined at the face of the solid support opposite of the face to which the ligand is attached, and the SPR angle of the single wavelength light is monitored before, during and/or after contacting the face to which the ligand is attached with the solution comprising the cleaned sample. The binding activity, in certain aspects, correlates with a concentration of an active form of the biotherapeutic in the solution. In exemplary aspects, the assay or method comprises comparing the change in the SPR angle, which may be reported as resonance units (RU), to a calibration curve to obtain a concentration of the active form of the biotherapeutic in the solution. Optionally, the calibration curve relates a concentration of the active form of the biotherapeutic within a range of about 0 ng/mL to about 100 ng/mL to a change in SPR angle. In various instances, the biotherapeutic comprises an Fc domain, optionally, wherein the biotherapeutic is an antibody, antibody fragment comprising an Fc, Fc fusion protein, or antibody protein product comprising an Fc domain. The ligand is in various aspects an Fc-binding protein optionally, Protein A, Protein G, or Protein L. In exemplary instances, the biotherapeutic comprises a CD3-binding domain, for example, a bispecific T-cell engager (BiTET™) molecule comprising a CD3-binding domain. In various instances, the ligand comprises a CD3 epitope that binds to the CD3-binding domain, optionally, the ligand is a CD3 protein. In exemplary aspects, the SPR-based assay is highly sensitive and has a very low limit of detection (LOD) for the active form of the biotherapeutic. For example, the LOD of the SPR-based assay, in various aspects, is less than about 20 ng/mL, optionally, less than about 15 ng/mL. In various instances, the LOD for the active form of the biotherapeutic is about 13.0 ng/mL or less, optionally, less than or about 10 ng/mL, less than or about 8 ng/mL, or less than or about 6.0 ng/mL. In various instances, the cleaning validation assay detects very low (e.g., less than 1 μg) concentrations of the active biotherapeutic, which detected concentrations are then used to calculate the % degradation achieved by the cleaning procedure. In various aspects, the SPR-based assay detects very low (e.g., less than 1 μg/mL) concentrations of the active biotherapeutic and demonstrates greater than about 99.99% degradation of the biotherapeutic. In various aspects, the cleaning validation assay demonstrates greater than about 99.999% degradation of the biotherapeutic, optionally, greater than about 99.9999% degradation. In exemplary embodiments, the method comprises carrying out a bench-scale cleaning procedure which simulates a large-scale cleaning procedure on a sample comprising the biotherapeutic to obtain a cleaned sample and analyzing the binding activity of the cleaned sample to a ligand which binds to a biotherapeutic produced during the manufacturing process. In various aspects, the assay or method comprises one or more steps prior to determining the binding activity. Optionally, the cleaned sample is filtered through a filter before determining the binding activity. In various aspects, the assay or method comprises filtering the cleaned sample through a filter, e.g., a PES filter, to reduce the amount of precipitates and/or salt crystals in the cleaned sample and/or filtering the cleaned sample through a filter, e.g., a molecular weight cut-off (MWCO) filter, optionally, wherein the MWCO is about 30 kDa to about 50 kDa, to reduce the total volume of the cleaned sample and to increase a protein concentration of the cleaned sample. In various aspects, the cleaned sample is filtered through a 30 kDa-MWCO filter to increase the concentration of proteins having a molecular weight greater than or equal to 30 kDa. Optionally, the PES filter is a 0.2 μm PES filter. In some aspects, the biotherapeutic manufacturing process includes affinity chromatography, ion exchange chromatography, viral inactivation, viral filtration, ultrafiltration, diafiltration, or any combination thereof of a downstream purification process. Optionally, the affinity chromatography is a Protein A chromatography and/or the ion exchange chromatography is anion exchange or cation exchange chromatography, or a combination thereof.

BRIEF DESCRIPTION OF THE DRAWINGS

FIG. 1A is a schematic of a multiproduct manufacturing process wherein the production of a first biotherapeutic (red circles) is followed by production of a second biotherapeutic (green circles) and a full-scale cleaning procedure is carried out between production runs. In some instances, an amount of the first biotherapeutic is present in a batch of the second biotherapeutic. FIG. 1B is a schematic of a cleaning validation assay of a full-scale cleaning procedure, wherein a small-scale cleaning procedure is carried out on a sample comprising the first product to obtain a cleaned sample. The small-scale cleaning procedure comprises an alkaline wash, an acidic wash, and optionally steaming. The conditions of the steps of the small-scale cleaning procedure may be the same as the full-scale cleaning procedure in terms of, e.g., length of time for each step, concentration and/or pH of alkaline solution for alkaline wash, concentration and/or pH of acidic solution for acidic wash, lower temperatures for the high temperature step, and the like, or the conditions of the steps of the small-scale cleaning procedure may differ from the full-scale cleaning procedure and may have shorter times for one or more steps, lower concentrations of the base for the alkaline wash or lower concentrations of the acid for the acidic wash, or lower temperatures for the high temperature step. The cleaned sample is then analytically assayed to determine % degradation of the biotherapeutic and/or the concentration of the active form of the biotherapeutic. For a very high potent biotherapeutic, it must be demonstrated that >99.99% degradation of the active product was achieved by the cleaning procedure.

FIG. 3A is an illustration of a cleaned sample comprising protein analytes that bind to the ligand immobilized on the chip of the SPR instrument (specific binding) and protein analytes that bind to the chip without the ligand (non-specific binding). "Reducing Non-Specific Binding in Surface Plasmon Resonance Experiments" available at nicoyalife.com. FIG. 3B is a schematic of the cleaning validation assay comprising a small-scale cleaning procedure to obtain a cleaned sample, followed by filtering the cleaned sample through a PES filter and a MWCO filter and determining the binding activity of the cleaned, filtered sample in a SPR-based assay.

DETAILED DESCRIPTION

Figure 2:
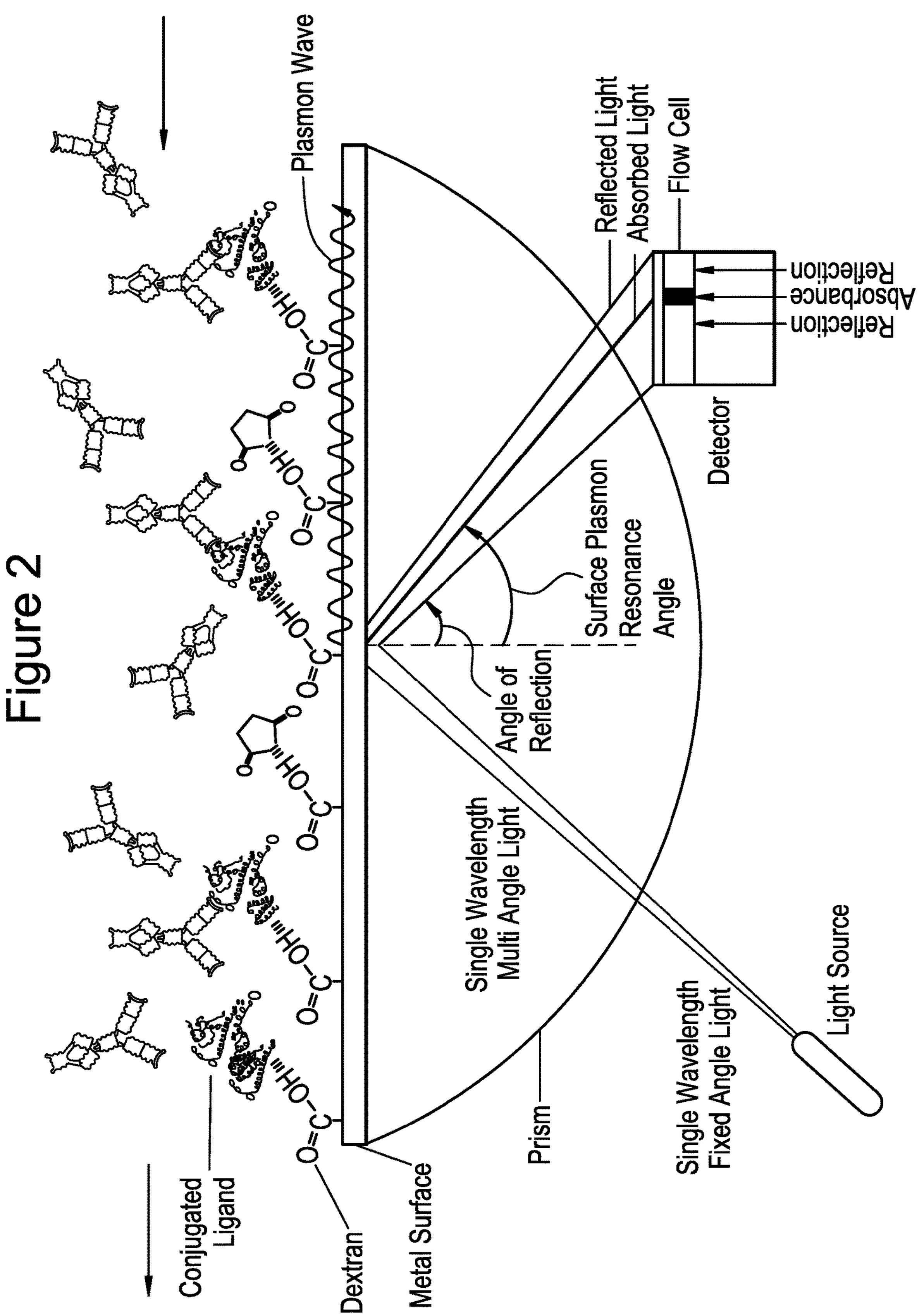
FIG. 2 is a schematic of an SPR-based assay detecting binding activity of the cleaned sample to a ligand immobilized or conjugated to a dextran-coated metal surface. On the face of the metal surface opposite of the ligands, a light source of a single wavelength shines at a fixed angle and/or multi angle. Some light reflects off of the metal surface and some light is absorbed, and a detector measures the change in the amount of the light absorbed vs. reflected before, during, and/or after a solution comprising the cleaned sample contacts the ligands. The amount of the light absorbed vs. reflected changes when the ligand binds to a residual biotherapeutic present in the cleaned sample. The biotherapeutic that binds to ligand represents the active form which is neither inactivated nor degraded during the cleaning procedure. SariSabban-Sabban, Sari (2011) *Development of an in vitro model system for studying the interaction of Equus caballus IgE with its high-affinity FcεRI receptor* (PhD thesis), The University of Sheffield.

The present disclosure provides a cleaning validation assay for a biotherapeutic manufacturing process. In exemplary aspects, the assay comprises determining the binding activity of a cleaned sample to a ligand which binds to the biotherapeutic produced by the biotherapeutic manufacturing process. In various aspects, the binding activity is determined by a surface plasmon resonance (SPR)-based assay. Optionally, the binding activity determined by the SPR-based assay correlates with a concentration of the biotherapeutic of the cleaned sample. Optionally, the cleaned sample is obtained by carrying out a small-scale cleaning procedure, which simulates a large-scale cleaning procedure, on a sample comprising the biotherapeutic.

The present disclosure also provides methods of validating a cleaning procedure of a biotherapeutic manufacturing process. In exemplary embodiments, the method comprises (i) carrying out a small-scale cleaning procedure, which simulates a large-scale cleaning procedure, on a sample comprising the biotherapeutic produced by the biotherapeutic manufacturing process, to obtain a cleaned sample, and (ii) determining the binding activity of the cleaned sample to a ligand which binds to the biotherapeutic, wherein the binding activity is determined by a surface plasmon resonance (SPR)-based assay.

Cleaning Procedure

In various aspects, the assays or methods comprise carrying out a cleaning procedure on a sample comprising the biotherapeutic produced by the biotherapeutic manufacturing process, to obtain a cleaned sample. Suitable cleaning procedures are known in the art. See, e.g., Technical Report No. 49, Points to Consider for Biotechnology Cleaning Validation, Parental Drug Association, Inc., 2010; and Gronberg and Hjorth (2018), supra). In various instances, the cleaning procedure comprises a pre-rinse, alkaline wash, water rinse, acidic wash, and/or final water rinse.

In various aspects, the cleaning procedure is a small-scale cleaning procedure, e.g., a bench-scale cleaning procedure, which simulates a large-scale cleaning procedure. Optionally, the small-scale cleaning procedure comprises the same conditions of the large-scale cleaning procedure. For example, if the small-scale cleaning procedure comprises an alkaline wash, an acidic wash, and steaming, the conditions of these steps of the small-scale cleaning procedure may be the same as the full-scale cleaning procedure in terms of, e.g., length of time for each step, concentration and/or pH of alkaline solution for alkaline wash, concentration and/or pH of acidic solution for acidic wash, lower temperatures for the high temperature step, and the like. Alternatively, the conditions of the steps of the small-scale cleaning procedure may differ from the full-scale cleaning procedure and may be considered as a worst-case scenario of the full-scale cleaning procedure. The small-scale cleaning procedure, for example, may have shorter times for one or more steps, lower concentrations of the base for the alkaline wash or lower concentrations of the acid for the acidic wash, or lower temperatures for the high temperature step. In various instances, the small-scale cleaning procedure comprises conditions similar to those of the large-scale cleaning procedure but has one or more cleaning steps missing altogether or has shortened times, lower temperatures, lower concentrations of cleaning agents, or any combination thereof, relative to the large-scale cleaning procedure. In various instances, the small-scale cleaning procedure simulates the worst-case scenario of the large-scale cleaning procedure. In exemplary aspects, the worst-case scenario of the large-scale cleaning procedure leads to the highest contamination or soil and/or highest amount of the biotherapeutic (in the active form, neither inactivated nor degraded). In exemplary aspects, the small-scale cleaning procedure is devoid of one or more steps that are carried out in the large-scale cleaning procedure, e.g., an initial rinse. In exemplary aspects, the small-scale cleaning procedure comprises a step carried out in the large-scale cleaning procedure but the step in the small-scale cleaning procedure is carried out for only a fraction of the time that the step is carried out in the large-scale cleaning procedure and/or at lower temperatures.

In various embodiments, the cleaning procedure, small-scale and/or large scale, comprises one or more steps to inactivate or degrade a biotherapeutic. In various instances, the cleaning procedure comprises at least one degradation step and/or at least one inactivation step purposed for degrading and/or inactivating the biotherapeutic. In exemplary aspects, the cleaning procedure comprises an alkaline wash, an acidic wash, a high temperature step, or any combination thereof.

In various aspects, the high temperature step comprises steaming, optionally, a steaming in place (SIP). In various instances, the high temperature step occurs at a temperature greater than 100 degrees C. In various instances, the high temperature step occurs at a temperature greater than 110 degrees C. or greater than 120 degrees C., optionally, in an autoclave. In various instances, the high temperature step is combined with the alkaline wash and/or the acidic wash. In various aspects, the alkaline wash and/or the acidic wash occur at a high temperature, optionally, a temperature greater than 100 degrees C. Alternatively, the alkaline wash and/or the acidic wash occur at an ambient temperature, optionally, a temperature of about 20 degrees C. to about 30 degrees C. In various instances, the alkaline wash occurs at a pH of 11 or higher and/or the acidic wash occurs at a pH less than 3. In various instances, the alkaline wash occurs at a pH of 11 or higher, e.g., 11, 11.5, 12, 12.5, 13, 13.5, 14. In various aspects, the alkaline wash comprises contacting a sample with sodium hydroxide or other caustic agent, such as sodium hydroxide, potassium hydroxide, CIP-100, or a combination thereof, optionally, at a concentration of about 0.1 N. In some aspects, the concentration is about 1 M or higher. In various aspects, the alkaline wash is carried out for at least 1 minute, optionally, 2 minutes, 3 min, 4 min, 5 min, 6 min, 7 min, 8 min, 9 min, or 10 min, or less than 20 min, in the small-scale cleaning procedure. In various aspects, the acidic wash occurs at a pH less than 3, e.g., 3, 2.5, 2.0, 1.5, 1. In various aspects, the alkaline wash comprises contacting a sample with phosphoric acid ($H_3PO_4$) or other acidic agent, e.g., acetic acid, optionally, at a concentration of at least 0.1 N to about 3N or 3 M. In various aspects, the acidic wash is carried out for at least 2 minutes in the small-scale cleaning procedure. The alkaline wash and/or the acidic wash optionally occurs with shaking. In various aspects, 6 M guanidium hydrochloride and/or 8 M urea is used. Optionally, the cleaning procedure comprises use of isopropanol or ethanol and/or sodium chloride. The cleaning procedure comprises in exemplary instances a neutralization after the alkaline wash and/or the acidic wash. In the bench scale study, the pH neutralization comprises changing the pH to a pH of about 5 to about 7.

SPR-Based Assay and LOD

The cleaning validation assay and the methods of the present disclosure in exemplary embodiments comprise determining the binding activity of a cleaned sample to a ligand which binds to the biotherapeutic produced by the biotherapeutic manufacturing process. In various instances, the binding activity is determined by a surface plasmon resonance (SPR)-based assay, which correlates the binding activity to a concentration of the biotherapeutic. Surface Plasmon Resonance assays are known in the art. See, e.g., Guo, J Biophotonics 5(7) 483-501 (2012); and Boozer et al., Current Opin Biotech 17: 400-405 (2006). In various aspects, the ligand is attached to a face of a solid support. In various instances, the assay or method comprises contacting the face to which the ligand is attached with a solution comprising the cleaned sample. Optionally, the solid support comprises a metal surface and a dextran coating. In various instances, a single wavelength light shines at the face of the solid support opposite of the face to which the ligand is attached and the SPR angle of the single wavelength light is monitored before, during and after contacting the face to which the ligand is attached with the solution comprising the cleaned sample. One or more of the SPR-based assay is carried out on an SPR instrument, such as a Biacore SPR system (Biacore 8K+, Biacore 8K, Biacore S200, Biacore T200, Biacore X100, Biacore C) or Carterra LSA.

In various aspects, the binding activity as determined through the SPR-based assay correlates with a concentration of an active form of the biotherapeutic in the solution. In various instances, the assay or method further comprises comparing the binding activity which in various aspects is reported as the change in the SPR angle (optionally as resonance units (RU)) to a calibration curve which correlates a change in the SPR angle (optionally in RU) to a concentration of the active form of the biotherapeutic, to determine the concentration of the biotherapeutic of the cleaned sample. The term "calibration curve" as used herein is synonymous with "standard curve". The calibration curve in exemplary aspects, relates a concentration of the active form of the biotherapeutic within a range of about 0 ng/mL to about 100 ng/mL to a change in SPR angle. In exemplary aspects, the SPR-based assay is highly sensitive and has a very low limit of detection (LOD) for the active form of the biotherapeutic. For instance, the LOD of the SPR-based assay may be less than about 20 ng/mL, optionally, less than about 15 ng/mL. In various instances, the LOD for the active form of the biotherapeutic is less than or about 13.0 ng/mL, less than or about 10 ng/mL, less than or about 8 ng/mL, or less than or about 6.0 ng/mL. The detected concentration of the biotherapeutic SPR-based assay may be used to calculate the % degradation of the biotherapeutic achieved by the cleaning procedure. In various aspects, the detected concentration of the biotherapeutic SPR-based assay is very low and the calculated % degradation is very high (e.g., greater than 99.99%). In various instances, the % degradation is calculated using the following equation:

$$\%\ \text{Degradation} = 1 - \frac{(\text{Concentration of the Biotherapeutic})}{650\ \mu g} * 100\%$$

wherein "concentration of the biotherapeutic" is the concentration as determined by the SPR-based assay and the calibration curve. Accordingly, in various instances, the cleaning validation assay demonstrates greater than about 99.99% degradation of the biotherapeutic achieved by the cleaning procedure. In various aspects, the cleaning validation assay demonstrates greater than about 99.999% degradation of the biotherapeutic achieved by the cleaning procedure, optionally, greater than about 99.9999% degradation of the biotherapeutic achieved by the cleaning procedure.

The assays and methods of the present disclosure are not limited to the type of biotherapeutic and accordingly the assays and methods of the present disclosure are not limited to the type of ligand. The ligand which binds to the biotherapeutic may be any ligand which can be attached, linked or conjugated to a face of the solid support. Desirably, the ligand specifically binds to biotherapeutic with high affinity to, e.g., reduce non-specific binding. In exemplary aspects, the biotherapeutic is a protein and the ligand is an antibody that binds to the protein. In various instances, the biotherapeutic comprises an Fc domain, optionally, wherein the biotherapeutic is an antibody, antibody fragment comprising an Fc domain, antibody protein product comprising an Fc domain, or an Fc fusion protein, and optionally, the ligand is an Fc-binding protein optionally, Protein A, Protein G, or Protein L. In various aspects, the biotherapeutic is a bispecific T-cell engager (BiTE™) molecule comprising a CD3-binding domain. Optionally, the ligand comprises a CD3 epitope that binds to the CD3-binding domain, e.g., a CD3 protein.

Additional Steps

With regard to the cleaning validation assays and methods of the invention, the assays and/or methods may include additional steps. For example, the method may include repeating one or more of the recited step(s) of the method. Accordingly, in exemplary aspects, the method comprises re-determining the binding activity of the cleaned sample to the ligand. In exemplary instance, the method comprises carrying out the small-scale cleaning procedure more than once or carrying out more than one small scale cleaning procedures wherein each procedure differs from the other procedures by way of time and/or temperature of one or more cleaning steps and/or by presence or absence of one or more cleaning steps and/or by concentration of one or more cleaning agents. Optionally, prior to the cleaning procedure, there is a dirty hold time (DHT) carried out at ambient or high humidity conditions. As used herein, DHT refers to the time interval between the end of use of equipment, i.e., drained equipment, at the end of the production of the first product and the start of cleaning procedure. In some aspects, the DHT is carried out in a humidity chamber. In alternative aspects, the DHT is carried out at ambient conditions, e.g., about 24 hours to about 120 hours in humidity of <35% RH or at high humidity conditions, e.g., about 24 hrs to about 120 hrs DHT in humidity chamber of >35% RH.

In various instances, the cleaned sample is processed prior to the determining step. In exemplary instances, the cleaned sample is filtered through a filter before determining the binding activity. The assay or method in various aspects comprises filtering the cleaned sample through a filter to reduce the amount of precipitates and/or salt crystals in the cleaned sample. The filter in some aspects is a polyethersulfone (PES) filter, optionally, a 0.2 μm PES filter or a 0.22 μm PES filter. The assay or method in various instances comprises filtering the cleaned sample through a filter to concentrate the cleaned sample, to decrease the volume of the cleaned sample and/or to increase the protein concentration of the cleaned sample. Optionally, the filter is a molecular weight cut-off (MWCO) filter, optionally, wherein the MWCO is about 30 kDa to about 50 kDa. The assay or method in various aspects comprises filtering the cleaned sample through a PES filter and a MWCO filter having a MWCO at about 30 kDa to about 50 kDa. In exemplary aspects, the cleaned sample is filtered through a PES filter, e.g., a 0.22 μm PES filter, and a MWCO filter, e.g., a 30 kDa MWCO filter.

Biotherapeutics

The assays and methods of the present disclosure are not limited to the type of biotherapeutic. In exemplary aspects, the biotherapeutic comprises an amino acid. Optionally, the biotherapeutic is a polypeptide or protein. In various aspects, a ligand which binds to the biotherapeutic is known and is immobilized to a chip. In exemplary aspects, the biotherapeutic or the ligand is an antibody, or antigen-binding fragment of an antibody, or an antibody protein product. Such biotherapeutics are described in International Patent Application Publication No. WO2019/140196, the contents of which is incorporated herein by reference.

In exemplary aspects, the biotherapeutic is an antibody. As used herein, the term "antibody" refers to a protein having a conventional immunoglobulin format, comprising heavy and light chains, and comprising variable and constant regions. For example, an antibody may be an IgG which is a "Y-shaped" structure of two identical pairs of polypeptide chains, each pair having one "light" (typically having a molecular weight of about 25 kDa) and one "heavy" chain (typically having a molecular weight of about 50-70 kDa). An antibody has a variable region and a constant region. In IgG formats, the variable region is generally about 100-110 or more amino acids, comprises three complementarity determining regions (CDRs), is primarily responsible for antigen recognition, and substantially varies among other antibodies that bind to different antigens. See, e.g., Janeway et al., "Structure of the Antibody Molecule and the Immunoglobulin Genes", Immunobiology: The Immune System in Health and Disease, 4th ed. Elsevier Science Ltd./Garland Publishing, (1999).

Briefly, in an antibody scaffold, the CDRs are embedded within a framework in the heavy and light chain variable region where they constitute the regions largely responsible for antigen binding and recognition. A variable region comprises at least three heavy or light chain CDRs (Kabat et al., 1991, Sequences of Proteins of Immunological Interest, Public Health Service N.I.H., Bethesda, Md.; see also Chothia and Lesk, 1987, J. Mol. Biol. 196:901-917; Chothia et al., 1989, Nature 342: 877-883), within a framework region (designated framework regions 1-4, FR1, FR2, FR3, and FR4, by Kabat et al., 1991; see also Chothia and Lesk, 1987, supra).

Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Embodiments of the disclosure include all such classes or isotypes of antibodies. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. Accordingly, in exemplary embodiments, the antibody is an antibody of isotype IgA, IgD, IgE, IgG, or IgM, including any one of IgG1, IgG2, IgG3 or IgG4.

In various aspects, the antibody can be a monoclonal antibody or a polyclonal antibody. In exemplary instances, the antibody is a mammalian antibody, e.g., a mouse antibody, rat antibody, rabbit antibody, goat antibody, horse antibody, chicken antibody, hamster antibody, pig antibody, human antibody, and the like. In certain aspects, the recombinant glycosylated protein is a monoclonal human antibody.

An antibody, in various aspects, is cleaved into fragments by enzymes, such as, e.g., papain, pepsin, and/or gingipain K. Papain cleaves an antibody to produce two Fab fragments and a single Fc fragment. Pepsin cleaves an antibody to produce a F(ab')2 fragment and a pFc' fragment. In exemplary aspects, the biotherapeutic is an antigen-binding fragment of an antibody, e.g., a Fab, Fc, F(ab')2, or a pFc'. With regard to the assays and methods of the disclosure, the antibody may lack certain portions of an antibody, and may be an antibody fragment. In various aspects, the antibody fragment comprises at least a portion of the Fc region of an antibody.

The architecture of antibodies has been exploited to create a growing range of alternative antibody formats that spans a molecular-weight range of at least or about 12-150 kDa and a valency (n) range from monomeric (n=1), dimeric (n=2) and trimeric (n=3) to tetrameric (n=4) and potentially higher; such alternative antibody formats are referred to herein as "antibody protein products" or "antibody binding proteins".

Antibody protein products can be an antigen binding format based on antibody fragments, e.g., scFvs, Fabs and VHH/VH, which retain full antigen-binding capacity. The smallest antigen-binding fragment that retains its complete antigen binding site is the Fv fragment, which consists entirely of variable (V) regions. A soluble, flexible amino acid peptide linker is used to connect the V regions to a scFv (single chain fragment variable) fragment for stabilization of the molecule, or the constant (C) domains are added to the V regions to generate a Fab fragment [fragment, antigen-binding]. Both scFv and Fab are widely used fragments that can be easily produced in prokaryotic hosts. Other antibody protein products include disulfide-bond stabilized scFv (ds-scFv), single chain Fab (scFab), as well as di- and multimeric antibody formats like dia-, tria- and tetra-bodies, or minibodies (miniAbs) that comprise different formats consisting of scFvs linked to oligomerization domains. The smallest fragments are VHH/VH of camelid heavy chain Abs as well as single domain Abs (sdAb). The building block that is most frequently used to create novel antibody formats is the single-chain variable (V)-domain antibody fragment (scFv), which comprises V domains from the heavy and light chain (VH and VL domain) linked by a peptide linker of ~15 amino acid residues. A peptibody or peptide-Fc fusion is yet another antibody protein product. The structure of a peptibody consists of a biologically active peptide grafted onto an Fc domain. Peptibodies are well-described in the art. See, e.g., Shimamoto et al., mAbs 4(5): 586-591 (2012).

Other antibody protein products include a single chain antibody (SCA); a diabody; a triabody; a tetrabody; bispecific or trispecific antibodies, and the like. Bispecific antibodies can be divided into five major classes: BsIgG, appended IgG, BsAb fragments, bispecific fusion proteins and BsAb conjugates. See, e.g., Spiess et al., Molecular Immunology 67(2) Part A: 97-106 (2015).

In exemplary aspects, the biotherapeutic comprises any one of these antibody protein products (e.g., scFv, Fab VHH/VH, Fv fragment, ds-scFv, scFab, dimeric antibody, multimeric antibody (e.g., a diabody, triabody, tetrabody), miniAb, peptibody VHH/VH of camelid heavy chain antibody, sdAb, diabody; a triabody; a tetrabody; a bispecific or trispecific antibody, BsIgG, appended IgG, BsAb fragment, bispecific fusion protein, and BsAb conjugate) and comprises one or more Fc regions of an antibody.

The biotherapeutic may be an antibody protein product in monomeric form, or polymeric, oligomeric, or multimeric form. In certain embodiments in which the antibody comprises two or more distinct antigen binding regions fragments, the antibody is considered bispecific, trispecific, or multi-specific, or bivalent, trivalent, or multivalent, depending on the number of distinct epitopes that are recognized and bound by the antibody.

In various aspects, the biotherapeutic is a chimeric antibody or a humanized antibody. The term "chimeric antibody" is used herein to refer to an antibody containing constant domains from one species and the variable domains from a second, or more generally, containing stretches of amino acid sequence from at least two species. The term "humanized" when used in relation to antibodies refers to antibodies having at least CDR regions from a non-human source which are engineered to have a structure and immunological function more similar to true human antibodies than the original source antibodies. For example, humanizing can involve grafting CDR from a non-human antibody, such as a mouse antibody, into a human antibody. Humanizing also can involve select amino acid substitutions to make a non-human sequence look more like a human sequence.

Advantageously, the methods are not limited to the antigen-specificity of the antibody, antigen binding fragment, antibody protein product, chimeric antibody, or humanized antibody. Accordingly, the antibody, antigen binding fragment, antibody protein product, chimeric antibody, or humanized antibody has any binding specificity for virtually any antigen. In exemplary aspects, the antibody binds to a hormone, growth factor, cytokine, a cell-surface receptor, or any ligand thereof. In exemplary aspects, the antibody binds to a protein expressed on the cell surface of an immune cell. In exemplary aspects, the antibody binds to a cluster of differentiation molecule selected from the group consisting of: CD1a, CD1b, CD1c, CD1d, CD2, CD3, CD4, CD5, CD6, CD7, CD8, CD9, CD10, CD11A, CD11B, CD11C, CDw12, CD13, CD14, CD15, CD15s, CD16, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD45, CD45RO, CD45RA, CD45RB, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L, CD62P, CD63, CD64, CD65, CD66a, CD66b, CD66c, CD66d, CD66e, CD66f, CD68, CD69, CD70, CD71, CD72, CD73, CD74, CD75, CD76, CD79a, CD79β, CD80, CD81, CD82, CD83, CDw84, CD85, CD86, CD87, CD88, CD89, CD90, CD91, CDw92, CD93, CD94, CD95, CD96, CD97, CD98, CD99, CD100, CD101, CD102, CD103, CD104, CD105, CD106, CD107a, CD107b, CDw108, CD109, CD114, CD 115, CD116, CD117, CD118, CD119, CD120a, CD120b, CD121a, CDw121b, CD122, CD123, CD124, CD125, CD126, CD127, CDw128, CD129, CD130, CDw131, CD132, CD134, CD135, CDw136, CDw137, CD138, CD139, CD140a, CD140b, CD141, CD142, CD143, CD144, CD145, CD146, CD147, CD148, CD150, CD151, CD152, CD153, CD154, CD155, CD156, CD157, CD158a, CD158b, CD161, CD162, CD163, CD164, CD165, CD166, and CD182.

In exemplary aspects, the antibody, antigen binding fragment, antibody protein product, chimeric antibody, or humanized antibody is one of those described in U.S. Pat. No. 7,947,809 and U.S. Patent Application Publication No. 20090041784 (glucagon receptor), U.S. Pat. Nos. 7,939,070, 7,833,527, 7,767,206, and 7,786,284 (IL-17 receptor A), U.S. Pat. Nos. 7,872,106 and 7,592,429 (Sclerostin), U.S. Pat. Nos. 7,871,611, 7,815,907, 7,037,498, 7,700,742, and U.S. Patent Application Publication No. 20100255538 (IGF-1 receptor), U.S. Pat. No. 7,868,140 (B7RP1), U.S. Pat. No. 7,807,159 and U.S. Patent Application Publication No. 20110091455 (myostatin), U.S. Pat. Nos. 7,736,644, 7,628,986, 7,524,496, and U.S. Patent Application Publication No. 20100111979 (deletion mutants of epidermal growth factor receptor), U.S. Pat. No. 7,728,110 (SARS coronavirus), U.S. Pat. No. 7,718,776 and U.S. Patent Application Publication No. 20100209435 (OPGL), U.S. Pat. Nos. 7,658,924 and 7,521,053 (Angiopoietin-2), U.S. Pat. Nos. 7,601,818, 7,795,413, U.S. Patent Application Publication No. 20090155274, U.S. Patent Application Publication No. 20110040076 (NGF), U.S. Pat. No. 7,579,186 (TGE-β type II receptor), U.S. Pat. No. 7,541,438 (connective tissue growth factor), U.S. Pat. No. 7,438,910 (IL1-R1), U.S. Pat. No. 7,423,128 (properdin), U.S. Pat. Nos. 7,411, 057, 7,824,679, 7,109,003, 6,682,736, 7,132,281, and 7,807, 797 (CTLA-4), U.S. Pat. Nos. 7,084,257, 7,790,859, 7,335, 743, 7,084,257, and U.S. Patent Application Publication No. 20110045537 (interferon-gamma), U.S. Pat. No. 7,932,372 (MAdCAM), U.S. Pat. No. 7,906,625, U.S. Patent Application Publication No. 20080292639, and U.S. Patent Application Publication No. 20110044986 (amyloid), U.S. Pat. Nos. 7,815,907 and 7,700,742 (insulin-like growth factor I), U.S. Pat. Nos. 7,566,772 and 7,964,193 (interleukin-1β), U.S. Pat. Nos. 7,563,442, 7,288,251, 7,338,660, 7,626,012, 7,618,633, and U.S. Patent Application Publication No. 20100098694 (CD40), U.S. Pat. No. 7,498,420 (c-Met), U.S. Pat. Nos. 7,326,414, 7,592,430, and 7,728,113 (M-CSF), U.S. Pat. Nos. 6,924,360, 7,067,131, and 7,090, 844 (MUC18), U.S. Pat. Nos. 6,235,883, 7,807,798, and U.S. Patent Application Publication No. 20100305307 (epidermal growth factor receptor), U.S. Pat. Nos. 6,716,587, 7,872,113, 7,465,450, 7,186,809, 7,317,090, and 7,638,606 (interleukin-4 receptor), U.S. Patent Application Publication No. 20110135657 (BETA-KLOTHO), U.S. Pat. Nos. 7,887, 799 and 7,879,323 (fibroblast growth factor-like polypeptides), U.S. Pat. No. 7,867,494 (IgE), U.S. Patent Application Publication No. 20100254975 (ALPHA-4 BETA-7), U.S. Patent Application Publication No. 20100197005 and U.S. Pat. No. 7,537,762 (ACTIVIN RECEPTOR-LIKE KINASE-1), U.S. Pat. No. 7,585,500 and U.S. Patent Application Publication No. 20100047253 (IL-13), U.S. Patent Application Publication No. 20090263383 and U.S. Pat. No. 7,449,555 (CD148), U.S. Patent Application Publication No. 20090234106 (ACTIVIN A), U.S. Patent Application Publication No. 20090226447 (angiopoietin-1 and angiopoietin-2), U.S. Patent Application Publication No. 20090191212 (Angiopoietin-2), U.S. Patent Application Publication No. 20090155164 (C-FMS), U.S. Pat. No. 7,537,762 (activin receptor-like kinase-1), U.S. Pat. No. 7,371,381 (galanin), U.S. Patent Application Publication No. 20070196376 (INSULIN-LIKE GROWTH FACTORS), U.S. Pat. Nos. 7,267, 960 and 7,741,115 (LDCAM), U.S. Pat. No. 7,265,212 (CD45RB), U.S. Pat. No. 7,709,611, U.S. Patent Application Publication No. 20060127393 and U.S. Patent Application Publication No. 20100040619 (DKK1), U.S. Pat. No. 7,807, 795, U.S. Patent Application Publication No. 20030103978 and U.S. Pat. No. 7,923,008 (osteoprotegerin), U.S. Patent Application Publication No. 20090208489 (OV064), U.S. Patent Application Publication No. 20080286284 (PSMA), U.S. Pat. No. 7,888,482, U.S. Patent Application Publication No. 20110165171, and U.S. Patent Application Publication No. 20110059063 (PAR2), U.S. Patent Application Publication No. 20110150888 (HEPCIDIN), U.S. Pat. No. 7,939, 640 (B7L-1), U.S. Pat. No. 7,915,391 (c-Kit), U.S. Pat. Nos. 7,807,796, 7,193,058, and 7,427,669 (ULBP), U.S. Pat. Nos. 7,786,271, 7,304,144, and U.S. Patent Application Publication No. 20090238823 (TSLP), U.S. Pat. No. 7,767,793 (SIGIRR), U.S. Pat. No. 7,705,130 (HER-3), U.S. Pat. No. 7,704,501 (ataxin-1-like polypeptide), U.S. Pat. Nos. 7,695, 948 and 7,199,224 (TNF-α converting enzyme), U.S. Patent Application Publication No. 20090234106 (ACTIVIN A), U.S. Patent Application Publication No. 20090214559 and U.S. Pat. No. 7,438,910 (IL1-R1), U.S. Pat. No. 7,579,186 (TGE-β type II receptor), U.S. Pat. No. 7,569,387 (TNF receptor-like molecules), U.S. Pat. No. 7,541,438, (connective tissue growth factor), U.S. Pat. No. 7,521,048 (TRAIL receptor-2), U.S. Pat. Nos. 6,319,499, 7,081,523, and U.S. Patent Application Publication No. 20080182976 (erythropoietin receptor), U.S. Patent Application Publication No. 20080166352 and U.S. Pat. No. 7,435,796 (B7RP1), U.S. Pat. No. 7,423,128 (properdin), U.S. Pat. Nos. 7,422,742 and 7,141,653 (interleukin-5), U.S. Pat. Nos. 6,740,522 and 7,411,050 (RANKL), U.S. Pat. No. 7,378,091 (carbonic anhydrase IX (CA IX) tumor antigen), U.S. Pat. Nos. 7,318,925 and 7,288,253 (parathyroid hormone), U.S. Pat. No. 7,285,269 (TNF), U.S. Pat. Nos. 6,692,740 and 7,270, 817 (ACPL), U.S. Pat. No. 7,202,343 (monocyte chemo-attractant protein-1), U.S. Pat. No. 7,144,731 (SCF), U.S. Pat. Nos. 6,355,779 and 7,138,500 (4-1BB), U.S. Pat. No. 7,135,174 (PDGFD), U.S. Pat. Nos. 6,630,143 and 7,045, 128 (Flt-3 ligand), U.S. Pat. No. 6,849,450 (metalloproteinase inhibitor), U.S. Pat. No. 6,596,852 (LERK-5), U.S. Pat. No. 6,232,447 (LERK-6), U.S. Pat. No. 6,500,429 (brain-derived neurotrophic factor), U.S. Pat. No. 6,184,359 (epithelium-derived T-cell factor), U.S. Pat. No. 6,143,874 (neurotrophic factor NNT-1), U.S. Patent Application Publication No. 20110027287 (PROPROTEIN CONVERTASE SUBTILISIN KEXIN TYPE 9 (PCSK9)), U.S.

Patent Application Publication No. 20110014201 (IL-18 RECEPTOR), and U.S. Patent Application Publication No. 20090155164 (C-FMS). The above patents and published patent applications are incorporated herein by reference in their entirety for purposes of their disclosure of variable domain polypeptides, variable domain encoding nucleic acids, host cells, vectors, methods of making polypeptides encoding said variable domains, pharmaceutical compositions, and methods of treating diseases associated with the respective target of the variable domain-containing antigen binding protein or antibody.

In exemplary embodiments, the antibody, antigen binding fragment, antibody protein product, chimeric antibody, or humanized antibody is one of Muromonab-CD3 (product marketed with the brand name Orthoclone Okt3®), Abciximab (product marketed with the brand name Reopro®), Rituximab (product marketed with the brand name Mabl-hera®, Rituxan®), Basiliximab (product marketed with the brand name Simulect®), Daclizumab (product marketed with the brand name Zenapax®), Palivizumab (product marketed with the brand name Synagis®), Infliximab (product marketed with the brand name Remicade®), Trastuzumab (product marketed with the brand name Herceptin®), Alemtuzumab (product marketed with the brand name MabCampath®, Campath-1H®), Adalimumab (product marketed with the brand name Humira®), Tositumomab-I131 (product marketed with the brand name Bexxar®), Efalizumab (product marketed with the brand name Raptiva®), Cetuximab (product marketed with the brand name Erbitux®), l'Ibritumomab tiuxetan (product marketed with the brand name Zevalin®), I'Omalizumab (product marketed with the brand name Xolair®), Bevacizumab (product marketed with the brand name Avastin®), Natalizumab (product marketed with the brand name Tysabri®), Ranibizumab (product marketed with the brand name Lucentis®), Panitumumab (product marketed with the brand name Vectibix®), l'Eculizumab (product marketed with the brand name Soliris®), Certolizumab pegol (product marketed with the brand name Cimizia®), Golimumab (product marketed with the brand name Simponi®), Canakinumab (product marketed with the brand name Ilaris®), Catumaxomab (product marketed with the brand name Removab®), Ustekinumab (product marketed with the brand name Stelara®), Tocilizumab (product marketed with the brand name RoActemra®, Actemra®), Ofatumumab (product marketed with the brand name Arzerra®), Denosumab (product marketed with the brand name Prolia®), Belimumab (product marketed with the brand name Benlysta®), Raxibacumab, Ipilimumab (product marketed with the brand name Yervoy®), and Pertuzumab (product marketed with the brand name Perjeta®). In exemplary embodiments, the antibody, glycosylated Fc fragment, antibody protein product, chimeric antibody, or humanized antibody is one of anti-TNF alpha proteins such as adalimumab, infliximab, etanercept, golimumab, and certolizumab pegol; anti-TNF alpha antibodies such as adalimumab, infliximab, golimumab, and certolizumab pegol; anti-IL1beta antibodies such as canakinumab; anti-IL12/23 (p40) antibodies such as ustekinumab and briakinumab; and anti-IL2R antibodies, such as daclizumab. It will be understood that nonproprietary names of molecules described herein will include any innovator or biosimilar product comprising the molecule of that nonproprietary name. In exemplary embodiments, the antibody, glycosylated Fc fragment, antibody protein product, chimeric antibody, or humanized antibody is a biosimilar of one of the aforementioned antibodies.

In exemplary aspects, the antibody binds to a tumor associated antigen and is an anti-cancer antibody. Examples of suitable anti-cancer antibodies include, but are not limited to, anti-BAFF antibodies such as belimumab; anti-CD20 antibodies such as rituximab; anti-CD22 antibodies such as epratuzumab; anti-CD25 antibodies such as daclizumab; anti-CD30 antibodies such as iratumumab, anti-CD33 antibodies such as gemtuzumab, anti-CD52 antibodies such as alemtuzumab; anti-CD152 antibodies such as ipilimumab; anti-EGFR antibodies such as cetuximab; anti-HER2 antibodies such as trastuzumab and pertuzumab; anti-IL6 antibodies, such as siltuximab; and anti-VEGF antibodies such as bevacizumab; anti-IL6 receptor antibodies such as tocilizumab.

Figure 4A:
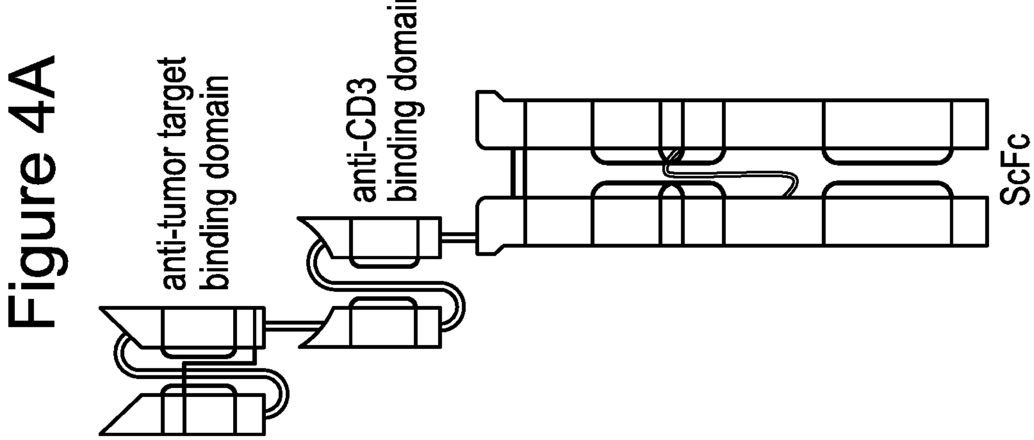
FIG. 4A is an illustration of a biotherapeutic comprising an anti-target binding domain, anti-CD3 binding domain and a single chain Fc (scFc) domain.

In some embodiments, the biotherapeutic is a BiTE® molecule. BiTE® molecules are engineered bispecific monoclonal antibodies which direct the cytotoxic activity of T cells against cancer cells. They are the fusion of two single-chain variable fragments (scFvs) of different antibodies, or amino acid sequences from four different genes, on a single peptide chain of about 55 kilodaltons. In some aspects, one of the scFvs binds to T cells via the CD3 receptor, and the other to a tumor cell via a tumor specific molecule. Blinatumomab (BLINCYTO®) is an example of a BiTE® molecule, specific for CD19. BiTE® molecules that are modified, such as those modified to extend their half-lives, can also be used in the disclosed methods. In various aspects, the BiTE® molecule comprises a single chain Fc (scFc). An exemplary biotherapeutic of this kind is pictured in FIG. 4A.

Potency of Biotherapeutics

The biotherapeutic in various aspects has a potency of at least about 100 μg. The biotherapeutic in various aspects is a monoclonal antibody and has a potency of ies, the ADE for the active form (e.g., neither inactivated nor degraded) is about 10 μg to about 100 μg and the calculated % degradation is about 85% to about 98%. For peptibodies, the ADE is about 1 μg to about 10 μg and the calculated % degradation is about 98.5% to about 99.8%. For biotherapeutics having high potency, the ADE is about 0.1 μg to about 1 μg and the calculated % degradation is about 99.85% to about 99.98%. For biotherapeutics having very high potency, the ADE is about 0.001 μg and the calculated % degradation is >99.99%.

Manufacturing Process

In exemplary aspects, the biotherapeutic manufacturing process is a multiproduct manufacturing process. The multiproduct manufacturing process in various instances produces different biotherapeutics in series using the same process equipment. In various aspects, the multiproduct manufacturing process produces at least two, at least three, at least four, at least five or more biotherapeutics in series using the same process equipment. In various instances, the multiproduct manufacturing process is not limited to a particular number of different biotherapeutics produced in series using the same equipment. In exemplary aspects, the biotherapeutic manufacturing process includes affinity chromatography, ion exchange chromatography, viral inactivation, viral filtration, ultrafiltration, diafiltration, or any combination thereof of a downstream purification process. Optionally, the affinity chromatography is a Protein A chromatography. The ion exchange chromatography is in certain aspects anion exchange or cation exchange chromatography, or a combination thereof.

The manufacturing process, in various aspects, comprises upstream or downstream processing involved in producing, purifying, and formulating a biotherapeutic, optionally, a protein, e.g., an antibody. Exemplary downstream processing includes any chromatography unit operation, including capture chromatography, intermediate chromatography, and/or polish chromatography unit operations; virus inactivation and neutralization; virus filtration; and/or final formulation.

The manufacturing process, in various aspects, comprises a harvest. As used herein the term "harvest" refers to cell culture media containing the biotherapeutic protein of interest being collected and separated at least from the cells of the cell culture. The harvest can be performed continuously. The harvest in some aspects is performed using centrifugation and can further comprise precipitation, filtration, and the like.

The downstream processing in various aspects is any processing which occurs after (or downstream of) the harvest, which in various aspects comprise(s): a dilution step, a filling step, a filtration step, a formulation step, a chromatography step, a viral filtration step, a viral inactivation step, or a combination thereof. the downstream processing comprises or consists of any processing which occurs after (or downstream of) the chromatography, and the downstream processing in various aspects comprise(s): a dilution, a filling, a filtration, a formulation, further chromatography, a viral filtration, a viral inactivation, or a combination thereof. In exemplary instances the further chromatography is an ion exchange chromatography (e.g., cation exchange chromatography or anion exchange chromatography).

Stages/types of chromatography used during downstream processing include capture or affinity chromatography which is used to separate the biotherapeutic from other proteins, aggregates, DNA, viruses and other such impurities. In exemplary instances, initial chromatography is carried out with Protein A (e.g., Protein A attached to a resin). Intermediate and polish chromatography in various aspects further purify the recombinant protein, removing bulk contaminants, adventitious viruses, trace impurities, aggregates, isoforms, etc. The chromatography can either be performed in bind and elute mode, where the recombinant protein of interest is bound to the chromatography medium and the impurities flow through, or in flow-through mode, where the impurities are bound and the recombinant protein flows through. Examples of such chromatography methods include ion exchange chromatography (IEX), such as anion exchange chromatography (AEX) and cation exchange chromatography (CEX); hydrophobic interaction chromatography (HIC); mixed modal or multimodal chromatography (MM), hydroxyapatite chromatography (HA); reverse phase chromatography and gel filtration.

In various aspects, the downstream processing comprises viral inactivation. Enveloped viruses have a capsid enclosed by a lipoprotein membrane or "envelope" and are therefore susceptible to inactivation. The virus inactivation in various instances includes heat inactivation/pasteurization, pH inactivation, UV and gamma ray irradiation, use of high intensity broad spectrum white light, addition of chemical inactivating agents, surfactants, and solvent/detergent treatments.

In various aspects, the downstream processing comprises virus filtration. In various aspects, the virus filtration comprises removing non-enveloped viruses. In various aspects, the virus filtration comprises the use of micro- or nanofilters.

In various aspects, the downstream processing comprises one or more formulation steps. Following completion of the chromatography, the purified recombinant proteins are in various aspects buffer exchanged into a formulation buffer. In exemplary aspects, the buffer exchange is performed using ultrafiltration and diafiltration (UF/DF). In exemplary aspects, the recombinant protein is buffer exchanged into a desired formulation buffer using diafiltration and concentrated to a desired final formulation concentration using ultrafiltration. Additional stability-enhancing excipients in various aspects are added following a UF/DF formulation.

In exemplary embodiments, the manufacturing process comprises upstream processing which occurs prior to harvest and/or includes harvest. The manufacturing process comprises in some aspects generating host cells that express a biotherapeutic protein (e.g., antibody). The host cells, in some aspects, are prokaryotic host cells, e.g., *E. coli* or *Bacillus subtilis*, or the host cells, in some aspects, are eukaryotic host cells, e.g., yeast cells, filamentous fungi cells, protozoa cells, insect cells, or mammalian cells (e.g., CHO cells). Such host cells are described in the art. See, e.g., Frenzel, et al., *Front Immunol* 4: 217 (2013). For example, the manufacturing process comprises, in some instances, introducing into host cells a vector comprising a nucleic acid comprising a nucleotide sequence encoding the biotherapeutic protein, or a polypeptide chain thereof.

In exemplary aspects, the manufacturing process comprises maintaining cells in a cell culture. The cell culture may be maintained according to any set of conditions suitable for production of the biotherapeutic protein. For example, in some aspects, the cell culture is maintained at a particular pH, temperature, cell density, culture volume, dissolved oxygen level, pressure, osmolality, and the like. In exemplary aspects, the cell culture prior to inoculation is shaken (e.g., at 70 rpm) at 5% $CO_2$ under standard humidified conditions in a $CO_2$ incubator. The cell culture is maintained in any one or more culture medium. In exemplary aspects, the cell culture is maintained in a medium suitable for cell growth and/or is provided with one or more feeding media according to any suitable feeding schedule. In exemplary embodiments, the type of cell culture is a fed-batch culture or a continuous perfusion culture. However, the manufacturing process of the disclosure are advantageously not limited to any particular type of cell culture.

EXEMPLARY EMBODIMENTS

Exemplary embodiments of the present disclosure are provided below.

E1. A method of assessing a cleaning procedure of a biotherapeutic manufacturing process, said method comprising analyzing the binding activity of a cleaned sample to a ligand which binds to a biotherapeutic produced during the manufacturing process.

E2. The method of embodiment 1, wherein the cleaned sample is obtained by carrying out the cleaning procedure on a sample comprising the biotherapeutic.

E3. The method of embodiment 2, wherein the cleaning procedure is a large-scale cleaning procedure.

E4. The method of embodiment 1, wherein the cleaned sample is obtained by carrying out a bench-scale cleaning procedure which simulates a large-scale cleaning procedure on a sample comprising the biotherapeutic.

E5. The method of any one of the preceding embodiments, wherein the cleaning procedure comprises one or more degradation and/or inactivation steps.

E6. The method of any one of the preceding embodiments, wherein the cleaning procedure comprises a dirty hold time (DHT), an alkaline wash, an acidic wash, a steaming step, or any combination thereof.

E7. The method of embodiment 6, wherein the DHT is carried out at ambient or high humidity conditions.

E8. The method of embodiment 6 or 7, wherein the steaming step occurs in an autoclave.

E9. The method of any one of embodiments 7 to 9, wherein the alkaline wash and/or the acidic wash occurs with shaking.

E10. The method of any one of embodiments 6 to 9, wherein the cleaning procedure comprises a neutralization step after the alkaline wash and/or the acidic wash.

E11. The method of any one of the preceding embodiments, further comprising carrying out the cleaning procedure on a sample comprising the biotherapeutic or carrying out a bench-scale cleaning procedure which simulates a large-scale cleaning procedure on a sample comprising the biotherapeutic.

E12. The method of any one of the preceding embodiments, comprising preparing the cleaned sample for the analyzing step, to obtain a prepared cleaned sample.

E13. The method of embodiment 12, wherein the cleaned sample is prepared for the analyzing step by filtering the cleaned sample through a filter.

E14. The method of embodiment 13, wherein the filtering reduces the amount of precipitates or salt crystals in the cleaned sample and/or concentrates the cleaned sample.

E15. The method of embodiment 13 or 14, wherein the filter is a polyethersulfone (PES) filter, optionally, a 0.2 μm PES filter.

E16. The method of any one of embodiments 13 to 15, wherein the filter has a molecular weight cut-off (MWCO) at about 30 kDa to about 50 kDa.

E17. The method of any one of embodiments 13 to 16, comprising filtering the cleaned sample through a PES filter and a filter having a MWCO at about 30 kDa to about 50 kDa.

E18. The method of any one of the preceding embodiments, wherein the binding activity is analyzed by a surface plasmon resonance (SPR)-based assay.

E19. The method of any one of the preceding embodiments, wherein the ligand is attached to a face of a solid support and a solution comprising the cleaned sample or prepared cleaned sample is contacted with the face of the solid support.

E20. The method of embodiment 19, wherein the solid support comprises a metal surface and a dextran coating.

E21. The method of embodiment 19 or 20, wherein a single wavelength light is shined at the at the face of the solid support opposite of the face to which the ligand is attached and monitoring the change in SPR angle of the single wavelength light.

E22. The method of embodiment 21, further comprising comparing the change in SPR angle to a calibration curve to obtain a concentration of the biotherapeutic in the solution optionally wherein the calibration curve relates a concentration of the biotherapeutic within a range of about 0 ng/mL to about 100 ng/mL to a change in SPR angle.

E23. The method of any one of the preceding embodiments, wherein the biotherapeutic comprises an Fc domain, optionally, wherein the biotherapeutic is an antibody.

E24. The method of embodiment 23, wherein the ligand is an Fc-binding protein optionally, Protein A.

E25. The method of any one of the preceding embodiments, wherein the biotherapeutic is a bispecific T-cell engager (BiTET™) molecule comprising a CD3-binding domain.

E26. The method of embodiment 25, wherein the ligand comprises a CD3 epitope that binds to the CD3-binding domain.

E27. The method of embodiment 26, wherein the ligand is a CD3 protein.

E28. The method of any one of the preceding embodiments, wherein the limit of detection for active biologic agent is less than 7.0 ng/mL, optionally, less than 6.0 ng/mL.

E29. The method of any one of the preceding embodiments, wherein the biotherapeutic manufacturing process includes affinity chromatography, ion exchange chromatography, viral inactivation, viral filtration, ultrafiltration, diafiltration, or any combination thereof of a downstream purification process.

E30. The method of embodiment 29, wherein the affinity chromatography is a Protein A chromatography.

E31. The method of embodiment 29, wherein the ion exchange chromatography is anion exchange or cation exchange chromatography, or a combination thereof.

E32. The method of any one of the preceding embodiments, wherein the biotherapeutic manufacturing process is a multiproduct manufacturing process.

The following examples are given merely to illustrate the present invention and not in any way to limit its scope.

EXAMPLES

Example 1

This example describes an exemplary cleaning procedure comprising inactivation and/or degradation.

An important consideration in multiproduct cleaning validation is to demonstrate that the carry-over of the previously manufactured Active Pharmaceutical Ingredient (API) into a batch of the subsequently manufactured product is acceptable from a predictive safety standpoint. If, however, the previously manufactured API becomes inactive during cleaning, the acceptance limits for cleaning validation should be based on the acceptable carryover of the inactivated protein (API).

Inactivation/Degradation studies were performed at bench-scale to demonstrate that the Drug Substance/Drug Product (DS/DP) is degraded and/or inactivated when exposed to the cleaning cycles used at the manufacturing site. See FIG. 1B. The bench scale studies were designed to simulate "worst-case" cleaning conditions compared to full scale conditions in terms of Soil (API) to Cleaning agent volume ratio. The bench scale studies were also designed to minimize dilution of the DS/DP. The remaining process conditions (temperature, concentration and time) were the same as full scale conditions. A summary of the steps and the conditions for each full scale and bench scale are provided below in Table 1.

TABLE 1

| Step | Parameter | Full Scale Condition | Bench Scale Condition |
|---|---|---|---|
| Dirty hold time | Humidity | Ambient | Ambient |
| | Duration | 72 hr | 72 hr |
| Initial rinse | Cleaning solution | PUR or WFI | N/A[1] |
| | Concentration | N/A | |
| | Temperature | 22° C. | |
| | Duration | 5 min | |
| Alkaline wash | Cleaning solution | CIP 100[2] | NaOH[3] |
| | Conductivity/ Concentration | 19 mS/cm | 0.1N (pH 12.8[3]) |
| | Temperature | 70-75° C. | 70° C.[4] |
| | Duration | 10 min | 10 min |

TABLE 1-continued

| Step | Parameter | Full Scale Condition | Bench Scale Condition |
|---|---|---|---|
| Acidic wash | Cleaning solution | CIP 200 | $H_3PO_4$[5] |
| | Conductivity/Concentration | 6 mS/cm | Titrate to pH 2.3[5] |
| | Temperature | 35-40° C. | 35° C. |
| | Duration | 5 min | 5 min |
| Steaming | Temperature | 121° C. | 121° C. |
| | Duration | 15 min | 15 min |

[1]The initial rinse was not simulated at small scale as this represents a worst-case scenario from the standpoint of cleaning/inactivation.
[2]CIP-100 is Potassium Hydroxide based detergent. CIP-100 is mentioned as it is the detergent used by the Manufacturing. At bench scale we use sodium hydroxide of similar pH.
[3]Sodium hydroxide (NaOH) was used at small scale to minimize matrix interference effects; the pH of the sodium hydroxide solution was prepared to match the pH of the CIP 100 solution at full scale. Note that at a given temperature, the effectiveness of an alkaline cleaning solution in inactivating a protein is determined primarily by the pH of the solution.
[4]The lower alkaline wash temperature was simulated at small scale as this represents a worst-case scenario from the standpoint of inactivation.
[5]Phosphoric acid (H3PO4) was used at small scale to minimize matrix interference effects; the pH of the phosphoric acid solution was prepared to match the pH of the CIP 200 solution at full scale. Note that at a given temperature, the effectiveness of an acidic cleaning solution in inactivating a protein is determined primarily by the pH of the solution.

In one study, a BiTE® molecule comprising a first binding domain that binds to B-cell Maturation Antigen (BCMA) and a second binding domain that binds to CD3 was used as the DS/DP. A calculated amount of the BiTE® molecule was spotted on a stainless-steel coupon and held for the known amount of dirty hold time (DHT). DHT is the time interval between the spotting of coupons with process soil and the start of the laboratory cleaning procedure. The bench-scale DHT is meant to simulate the full-scale DHT, which is the time interval between the end of use of equipment, i.e., drained equipment, and the start of cleaning.

To prepare for the alkaline wash, a shaker bath was charged with 15 L of deionized (DI) water and heated to 70° C.±2° C., and the shaker speed was set to 10 cm/sec. The container of 0.1 NaOH was heated to 70° C. in the bath. The BiTE® molecule-spotted coupon was placed in a clean sterile glass bottle with the soil side (spotted side) facing upwards. A calculated amount of the heated 0.1 N NaOH was spiked into the glass bottle which was then placed in the shaker bath at 70° C. for 10 minutes. Without being bound by theory, degradation of protein (DS/DP) occurred during this time due to the extreme pH conditions.

An acidic wash was carried out by titrating the contents of the glass bottle to a pH of 7.0±0.2 with phosphoric acid ($H_3PO_4$). Without being bound by theory, the acidic wash quenched the degradation reaction by neutralizing the pH. Half the amount of the degraded material was stored for analysis and the other half was autoclaved at 121° C. for 15 minutes to simulate steaming conditions. The quantities and concentrations of the above solutions at each step were recorded. The initial rinse of the full-scale cleaning process was not simulated at small scale as this represents a worst-case scenario from the standpoint of cleaning/inactivation. Also, the initial rinse was skipped to avoid dilution of the protein in the cleaning agents.

Example 2

This example describes an exemplary quantitative binding assay for evaluating the extent of inactivation/degradation of a DS/DP.

A highly sensitive analytical method is needed to demonstrate the inactivation and/or degradation of the DS/DP in the samples. The concentration of the residual DS/DP after treatment (inactivation/degradation) is expected to be extremely low, e.g., nanogram/ml or picogram/ml, and thus measuring such a low concentration requires an analytical method with a limit of detection (LOD) below 10 ng/mL. Because silver staining is qualitative in nature and cannot achieve such a level of sensitivity, it cannot be used to detect the DS/DP after treatment, and thus another analytical method is needed.

The use of a surface plasmon resonance (SPR)-based method using a SPR-based instrument, e.g., GE Biacore T200, Biacore T100, Biacore 4000, Biacore S51, was evaluated to determine if this method is sensitive enough to quantify the concentration of the DS/DP after treatment (inactivation/degradation). In SPR-based methods, ligands which bind to the analyte (DS/DP) are immobilized onto a sensor chip. The chip is conditioned, and the analyte is injected into the SPR-based instrument which passes the analyte (in solution) over the sensor chip. Binding of the analyte to the ligand immobilized on the sensor chip causes a light angle change which is captured by a detector of the SPR-based instrument and this response is measured in resonance units (RU). The RU is directly proportional to the concentration of the analyte on the surface of the sensor chip. Without being bound by theory, in this method, only DS/DP that was not degraded/inactivated binds to the ligand.

A standard curve or calibration curve is made using samples comprising known concentrations of analyte (DS/DP). The standard curve plots RU as a function of analyte (DS/DP) concentration. The RU is proportional to the concentration of the analyte (DS/DP) in the sample. Linear regression of the standard curve is used to calculate the concentration of test samples comprising unknown amounts of analyte. —The Limit of Detection (LOD) and Limit of Quantification (LOQ) of the method is calculated from the calibration curve using the slope (S) and Standard error (steyx function in Excel), wherein LOD is equal to 3.3(Sy/S) and LOQ is equal to 10(Sy/S), wherein Sy=Standard Error of Y for given X (Steyx function); and S=Slope.

To evaluate the extent of inactivation/degradation of the BiTE® molecule described in Example 1, an SPR-based method was carried out on the cleaned samples of the BiTE® molecule obtained from Example 1. In this study, a CD3 antigen was used as the ligand. The ligand was immobilized on a CM5 sensor chip through amine coupling. The SPR-based instrument (Biacore T-200) was set up for 25 injections of samples and primed with 1× running buffer to remove air from the lines.

A standard curve using untreated DS/DP (BiTE® molecule) ranging in concentration from 0 ng/mL to 100 ng/mL was prepared. Briefly, BiTE® molecule samples, which were neither inactivated nor degraded, were diluted with varied volumes of 5% Intra Venous Bag Solution Stabilizer (IVSS) buffer to arrive at a series of samples ranging from 0 ng/mL to 100 ng/mL BiTE® molecule. IVSS is described in International Patent Application Publication No. WO2018/204907. The response (RU) was recorded for each sample concentration of known BiTE® molecule. The standard curve correlated concentration of the untreated DS/DP (BiTE® molecule) to RU (Resonance Units) (response measured on the y-axis). The LOD and LOQ calculated using the standard curve was 8.78 ng/ml and 29 ng/ml, respectively.

The test samples comprising the treated (inactivated/degraded) BiTE® molecule to be analyzed by the SPR-based assay were prepared in triplicate to contain the DS/DP at one of three different concentrations: (1) at 100 ng/mL, (2) 1:1 dilution and (3) undiluted sample. To obtain test samples of (1), the cleaned sample from the bench-scale study was diluted to a final concentration of 100 ng/ml. Prior to dilution to 100 ng/mL, the concentration of the samples at each step of the bench-scale study was calculated based on the starting concentration of the DS/DP (spotted on the coupon) and the volumes of each reagent used during the bench-scale (small-scale) cleaning procedure. To obtain test samples of (2), equal volumes of the cleaned sample and IVSS solution were combined. To obtain test samples of (3) cleaned sample obtained from the bench scale study were prepared without any dilution or change in volume.

The run method settings used on the Biacore instrument were the same for the test samples as for the standard curve and are provided in Table 2.

TABLE 2

| Biacore Run Method Settings | |
|---|---|
| Sample Settings | |
| Contact Time | 12 min |
| Dissociation Time | 15 s |
| Flow rate | 20 μl per min |
| Flow path | both |

TABLE 2-continued

| Biacore Run Method Settings | |
|---|---|
| Regeneration Settings | |
| Contact Time | 15 s |
| Flow rate | 20 μl per min |
| Flow path | both |
| Detection Setting | |
| Flow path | 2-1 (or 4-3 if immobilization was on flow cell #4) |
| Biacore Temperature Settings (° C.) | |
| Analysis | 25 |
| Samples | 10 |

Table 3 provides the data for the BiTE® molecule test samples. In Table 3 (and in all tables described in subsequent tables, unless noted otherwise), "Prepared Concentration/Calculated Concentration" represents the calculated concentration of the DS/DP based on the starting concentration of the DS/DP (spotted on the coupon) and the volumes of each reagent used, "Measured Concentration" represents the concentration of the active BiTE® molecule as determined by the SPR-based method and the calibration curve, and "% Degradation" was calculated by dividing the value in column B by the value in column A multiplying by 100% then subtracting from 100. The positive control was DS/DP sample diluted to Concentration of 100 ng/ml and never exposed to cleaning process, and the negative control was a solution of the cleaning agents without any DS/DP neutralized to pH 7.0±0.2.

TABLE 3

| Sample | A Prepared Concentration/Calculated Concentration of the sample, ng/mL | B Measured Concentration ng/mL | C % Degradation from actual Sample concentration |
|---|---|---|---|
| Positive Control Replicate 1 | 100 | 114.1 | N/A |
| Positive Control Replicate 2 | 100 | 95.1 | N/A |
| Positive Control Replicate 3 | 100 | 70 | N/A |
| Negative Control Replicate 1 | 0 | 0 | N/A |
| Negative Control Replicate 2 | 0 | 0 | N/A |
| Negative Control Replicate 3 | 0 | 0 | N/A |
| Cleaned Sample [100 ng/mL] Replicate 1 | 100 | 8.7798* | 97.21 |
| Cleaned Sample [100 ng/mL] Replicate 2 | 100 | 8.7798* | 97.21 |
| Cleaned Sample [100 ng/mL] Replicate 3 | 100 | 8.7798* | 97.21 |
| Cleaned Sample-Diluted 1:1 Replicate 1 | 9677.5 | 13.1 | 99.87 |
| Cleaned Sample-Diluted 1:1 Replicate 2 | 9677.5 | 8.4* | >99.91 |
| Cleaned Sample-Diluted 1:1 Replicate 3 | 9677.5 | 7.1* | >99.93 |
| Cleaned Sample-Undiluted Replicate 1 | 19400 | 16.4 | 99.916 |
| Cleaned Sample-Undiluted Replicate 2 | 19400 | 11.6 | 99.940 |
| Cleaned Sample-Undiluted Replicate 3 | 19400 | 11.6 | 99.940 |

*The measurement recorded was obtained using linear regression of the standard curve and was lower than the LOD (8.78 ng/ml). Thus, the LOD was used to calculate the % degradation in column C. Thus, the LOD was used to calculate the % degradation in column C and the actual % degradation is at least the % degradation indicated in column C.

As shown in Table 3, the SPR-based method detected concentrations of the active form of the BiTE® molecule below the LOD (8.78 ng/mL). Using the LOD value in the % degradation calculations (for column C), at least 99.93% degradation of the DS/DP (BiTE® molecule) was achieved through the bench-scale cleaning procedure comprising the inactivation/degradation described in Example 1. These results support that the SPR-based method was sensitive enough to quantify the concentration of the DS/DP after treatment (inactivation/degradation).

Example 3

This example demonstrates another exemplary cleaning validation assay for a biotherapeutic manufacturing process.

The cleaning procedure comprising inactivation and/or degradation described in Example 1 was performed with the same BiTE® molecule described in Example 1. To determine if the sensitivity of the SPR-based assay demonstrated in Example 2 could be increased, a concentration step and/or filtration step was carried out with the cleaned samples after the cleaning procedure and prior to the SPR-based method. Briefly, the bench-scale cleaning procedure of Example 1 was carried out and the resulting cleaned samples were passed through a 0.22 μm polyethersulfone (PES) filter. Without being bound to theory, this filtration step removed precipitates and/or salt crystals from the cleaned samples without filtering any analyte (BiTE® molecule). A control sample of untreated sample was also passed through the PES filter as a control reference. In some instances, the PES-filtered samples were subsequently passed through a 30 kDa molecular weight cut off (MWCO) Amicon Filter Unit. In particular, the PES filtrate was placed above the Amicon Filter Unit and spun through the Amicon Filter Unit by centrifuging at 3000 rpm for 4 minutes. The MWCO filtrate retained molecules having a molecular weight ≥30K including analyte (BiTE® molecule). The concentration of these samples was calculated based on the volume retained from the supernatant. IVSS (5%) was added to the filtrate to achieve a final concentration of 5%.

A standard curve was prepared as essentially described in Example 2. The LOD was 5.24 ng/mL. The test samples were prepared in triplicate as described in Example 2 and subsequently injected into the Biacore instrument for analysis. Table 4 provides the data for the BiTE® molecule samples.

TABLE 4

| Sample | Prepared Concentration/Calculated Concentration of the sample, ng/mL | Measured Concentration ng/mL | % Degradation from actual Sample concentration |
|---|---|---|---|
| Positive Control Replicate 1 | 100 | 119.8 | N/A |
| Positive Control Replicate 2 | 100 | 129.73 | N/A |
| Positive Control Replicate 3 | 100 | 116.12 | N/A |
| Negative Control Replicate 1 | 0 | 0 | N/A |
| Negative Control Replicate 2 | 0 | 0 | N/A |
| Negative Control Replicate 3 | 0 | 0 | N/A |
| Inactivated Samples-PES Filter-30 K MWCO Replicate 1 | 163818 | 3.2076* | >99.99804% |
| Inactivated Samples-PES Filter-30 K MWCO Replicate 2 | 163818 | 1.9768* | >99.99879% |
| Inactivated Samples-PES Filter-30 K MWCO Replicate 3 | 163818 | 1.6872* | >99.99897% |

*The measurement recorded was obtained using linear regression of the standard curve and was lower than the LOD (5.24 ng/ml). Thus, the LOD was used to calculate the % degradation in column C and the actual % degradation is at least the % degradation indicated in column C.

As shown in Table 4, the SPR-based method detected concentrations of the active form of the BITE molecule below the LOD of 5.24 ng/ml. Using the LOD value in the % degradation calculations (for column C), greater than about 99.998-about 99.999% degradation of the BiTE molecule occurred. Because in this study lower amounts of residual BiTE® molecule were detected when the cleaned samples were concentrated and/or filtered, the cleaning validation assay was deemed as more sensitive with the inclusion of the concentration/filtration steps (compare the minimum measured concentration of Table 4 (below LOD of 5.24 ng/mL) to minimum measured concentration of Table 3 (below LOD of 8.78 ng/mL)). These results suggest that a cleaning validation assay comprising SPR-based quantitative analysis of concentrated/filtered cleaned samples comprising inactivated/degraded BiTE molecules leads to a LOD of 5.24 ng/ml, which is better than that achieved in Example 2 (LOD 8.78 ng/ml). Without being bound to theory, the added MWCO filtration step increased the concentration of the BiTE molecule in the cleaned samples approximately 4-fold.

Example 4

This example demonstrates validation of a bench-scale cleaning procedure comprising inactivation and/or degradation simulating the worst-case cleaning at full scale.

A bench-scale cleaning procedure comprising inactivation and/or degradation of the DS/DP was designed to simulate a worst-case scenario of a full-scale inactivation/degradation, as described in Example 1. In this study, the bench-scale cleaning procedure described in Table 1 was carried out with the same BiTE® molecule described in Example 1 with varied time lengths for the caustic wash. Samples were exposed to 30 seconds, 1 minute, 2 minutes, 3 minutes and 5 minutes of alkaline wash. Since the full-length alkaline wash in Table 1 was 10 minutes, the shorter times of the alkaline wash represented 5%, 10%, 20%, 30% and 50% of the full-length alkaline wash. A sample of the BiTE® molecule after each cleaning procedure was analyzed for binding activity as described in Example 2. Prior to the binding activity assay, the cleaned samples were filtered as described in Example 3.

The standard curve was prepared as described in Example 2. The LOD was 6.93 ng/mL. The test samples were prepared in triplicate as described in Example 2 and subsequently injected into the Biacore instrument for analysis. Table 5 provides the data for the BiTE® molecule samples.

TABLE 5

| Sample | Prepared Concentration/Calculated Concentration of the sample, ng/mL | Measured Concentration ng/mL | % Degradation from actual Sample concentration |
|---|---|---|---|
| Positive Control Replicate 1 | 100 | 89.8746 | N/A |
| Positive Control Replicate 2 | 100 | 110.2762 | N/A |
| Positive Control Replicate 3 | 100 | 102.6658 | N/A |
| Negative Control Replicate 1 | 0 | 0 | N/A |
| Negative Control Replicate 2 | 0 | 0 | N/A |
| Negative Control Replicate 3 | 0 | 0 | N/A |
| Drug substance exposed to 30 seconds of the cycle Replicate 1 | 44802.8 | 59.5 | 99.8672% |
| Drug substance exposed to 30 seconds of the cycle Replicate 2 | 44802.8 | 53.5 | 99.8805% |
| Drug substance exposed to 30 seconds of the cycle Replicate 3 | 44802.8 | 159.8 | 99.6433% |
| Drug substance exposed to 1 min of the cycle Replicate 1 | 44802.8 | <LOD | 99.9894% |
| Drug substance exposed to 1 min of the cycle Replicate 2 | 44802.8 | <LOD | 99.9951% |
| Drug substance exposed to 1 min of the cycle Replicate 3 | 44802.8 | <LOD | 99.9999% |
| Drug substance exposed to 2 min of the cycle Replicate 1 | 44802.8 | <LOD | >99.999% |
| Drug substance exposed to 2 min of the cycle Replicate 2 | 44802.8 | <LOD | >99.999% |
| Drug substance exposed to 2 min of the cycle Replicate 3 | 44802.8 | <LOD | >99.999% |
| Drug substance exposed to 3 min of the cycle Replicate 1 | 44802.8 | <LOD | >99.999% |
| Drug substance exposed to 3 min of the cycle Replicate 2 | 44802.8 | <LOD | >99.999% |
| Drug substance exposed to 3 min of the cycle Replicate 3 | 44802.8 | <LOD | >99.999% |
| Drug substance exposed to 5 min of the cycle Replicate 1 | 44802.8 | <LOD | >99.999% |
| Drug substance exposed to 5 min of the cycle Replicate 2 | 44802.8 | <LOD | >99.999% |
| Drug substance exposed to 5 min of the cycle Replicate 3 | 44802.8 | <LOD | >99.999% |

* The measurement recorded was obtained using linear regression of the standard curve and was lower than the LOD (6.93 ng/ml). Thus, the LOD was used to calculate the % degradation in column C and the actual % degradation is at least the % degradation indicated in column C.

Based on the above results, 99.9% degradation of the BiTE molecule was achieved with a 30-second exposure to caustic, 99.99% of the BiTE molecule was degraded with a 1-minute of caustic exposure and the concentration of the BiTE molecule was below the LOD of the method after 1 minute of exposure. These results support that 99.9% degradation/inactivation of the DS/DP is achieved with as little as a 30-second caustic wash and suggest the full-scale cleaning cycle comprising a 10-minute caustic exposure (alkaline wash) leads to a significantly higher % degradation, e.g., 99.999% inactivation/degradation of the DS/DP. Thus, cleaning processes comprising such a caustic exposure avoid cross contamination of one product during the production of another.

Example 5

This example describes an exemplary cleaning validation assay carried out on another biotherapeutic.

The inactivation/degradation described in Example 1 was carried out with a second BiTE® molecule comprising a first binding domain that binds to CD33 and a second binding domain that binds to CD3. Briefly, a calculated amount of the BiTE® molecule was spotted on a stainless-steel coupon and held for the DHT. The BiTE® molecule-spotted coupon was placed in a sterile vial/bottle with the soil facing upwards and a calculated amount of 0.1 N NaOH was spiked into the glass bottle and placed in the shaker bath at 70° C. for 10 minutes. The vial was then titrated to a pH of 7.0±0.2 with phosphoric acid (H3PO4). Half the amount of the degraded material was stored for analysis and the rest was then autoclaved at 121° C. for 15 minutes to simulate steaming conditions. The SPR-based assay of Example 2 was carried out on the cleaned samples and the data are provided in Table 6.

A standard curve was prepared as described in Example 2 and the LOD was 3.42 ng/mL.

TABLE 6

| Sample | Prepared Concentration/Calculated Concentration of the sample, ng/mL | Measured Concentration* ng/mL | % Degradation from actual Sample concentration |
|---|---|---|---|
| Positive Control Replicate 1 | 25 | 38.04 | N/A |
| Positive Control Replicate 2 | 25 | 38.24 | N/A |
| Positive Control Replicate 3 | 25 | 39.06 | N/A |
| Negative Control Replicate 1 | 0 | 0 | N/A |
| Negative Control Replicate 2 | 0 | 0 | N/A |
| Negative Control Replicate 3 | 0 | 0 | N/A |
| Inactivated Sample Undiluted Replicate 1 | 16774.19 | 1.516 | 99.99 |
| Inactivated Sample Undiluted Replicate 2 | 16774.19 | 1.516 | 99.99 |
| Inactivated Sample Undiluted Replicate 3 | 16774.19 | 1.516 | 99.99 |
| Inactivated Sample-Diluted 1:1 Replicate 1 | 8387.1 | 1.516 | 99.98 |
| Inactivated Sample-Diluted 1:1 Replicate 2 | 8387.1 | 1.516 | 99.98 |
| Inactivated Sample-Diluted 1:1 Replicate 3 | 8387.1 | 1.516 | 99.98 |

*Some measurements were obtained using linear regression of the standard curve and were determined as lower than the LOD (3.42 ng/ml). Thus, the LOD was used to calculate the % degradation in column C and the actual % degradation is at least the % degradation indicated in column C.

As shown in Table 6, the SPR-based method detected concentrations of the active form of the BiTE® molecule which were below the LOD of 3.42 ng/mL. Using the LOD, at least about 99.98-99.99% degradation of the BiTE® molecule was achieved through the bench-scale cleaning procedure comprising the inactivation/degradation.

The same steps described in Example 3 were carried out with samples comprising the second BiTE® molecule. Briefly, cleaned samples obtained by carrying out the bench-scale cleaning procedure comprising the inactivation/degradation of Example 1 were filtered through a PES filter followed by filtration with a 30 kDa MWCO filter. The SPR-based method was carried out as described in Example 3. The results are provided in Table 7.

A standard curve was prepared as described in Example 2 and the LOD was 11.16 ng/mL.

TABLE 7

| Sample | Prepared Concentration/Calculated Concentration of the sample, ng/mL | Measured Concentration* ng/mL | % Degradation from actual Sample concentration |
|---|---|---|---|
| Positive Control Replicate 1 | 27 | 40.34 | N/A |
| Positive Control Replicate 2 | 27 | 40.83 | N/A |
| Positive Control Replicate 3 | 27 | 47.06 | N/A |
| Negative Control Replicate 1 | 0 | 0 | N/A |
| Negative Control Replicate 2 | 0 | 0 | N/A |
| Negative Control Replicate 3 | 0 | 0 | N/A |
| Inactivated Post Neutralized Samples-PES Filter-30 K MWCO Replicate 1 | 218247 | 6.5596 | 99.99 |
| Inactivated Post Neutralized Samples-PES Filter-30 K MWCO Replicate 2 | 218247 | 6.9893 | 99.99 |
| Inactivated Post Neutralized Samples-PES Filter-30 K MWCO Replicate 3 | 218247 | 7.0968 | 99.99 |

*Some measurements were obtained using linear regression of the standard curve and were determined as lower than the LOD (11.16 ng/ml). Thus, the LOD was used to calculate the % degradation in column C and the actual % degradation is at least the % degradation indicated in column C As shown in Table 7, the SPR-based method detected as little as 6.5596 ng/mL of the active form of the BiTE® molecule, supporting a % degradation of at least about 99.99% of the BiTE® molecule achieved through the bench-scale cleaning procedure comprising the inactivation/degradation.

The same experiment described in Example 4 was carried out with the second BiTE molecule and the results are shown in Table 8. A standard curve was prepared as described in Example 2 and the LOD was 12.52 ng/mL.

TABLE 8

| Sample | Prepared Concentration/Calculated Concentration of the sample, ng/mL | Measured Concentration* ng/mL | % Degradation from actual Sample concentration |
|---|---|---|---|
| Positive Control Replicate 1 | 100 | 89.8746 | N/A |
| Positive Control Replicate 2 | 100 | 110.2762 | N/A |
| Positive Control Replicate 3 | 100 | 102.6658 | N/A |
| Negative Control Replicate 1 | 0 | 0 | N/A |
| Negative Control Replicate 2 | 0 | 0 | N/A |
| Negative Control Replicate 3 | 0 | 0 | N/A |
| Drug substance exposed to 30 seconds of the cycle Replicate 1 | 23316.2945 | 15.2587 | 99.93% |
| Drug substance exposed to 30 seconds of the cycle Replicate 2 | 23316.2945 | 14.9717 | 99.94% |
| Drug substance exposed to 30 seconds of the cycle Replicate 3 | 23316.2945 | 17.0763 | 99.93% |
| Drug substance exposed to 1 min of the cycle Replicate 1 | 23316.2945 | <LOD | 99.98% |
| Drug substance exposed to 1 min of the cycle Replicate 2 | 23316.2945 | <LOD | 99.98% |
| Drug substance exposed to 1 min of the cycle Replicate 3 | 23316.2945 | <LOD | 99.99% |
| Drug substance exposed to 2 min of the cycle Replicate 1 | 23316.2945 | <LOD | >99.99% |
| Drug substance exposed to 2 min of the cycle Replicate 2 | 23316.2945 | <LOD | >99.99% |
| Drug substance exposed to 2 min of the cycle Replicate 3 | 23316.2945 | <LOD | >99.99% |
| Drug substance exposed to 3 min of the cycle Replicate 1 | 23316.2945 | <LOD | >99.99% |
| Drug substance exposed to 3 min of the cycle Replicate 2 | 23316.2945 | <LOD | >99.99% |
| Drug substance exposed to 3 min of the cycle Replicate 3 | 23316.2945 | <LOD | >99.99% |
| Drug substance exposed to 5 min of the cycle Replicate 1 | 23316.2945 | <LOD | >99.99% |
| Drug substance exposed to 5 min of the cycle Replicate 2 | 23316.2945 | <LOD | >99.99% |
| Drug substance exposed to 5 min of the cycle Replicate 3 | 23316.2945 | <LOD | >99.99% |

*Some measurements were obtained using linear regression of the standard curve and were determined as lower than the LOD (12.52 ng/ml). Thus, the LOD was used to calculate the % degradation in column C and the actual % degradation is at least the % degradation indicated in column C.

As supported by the data in Table 8, the concentration of the cleaned sample was below the LOD (12.52 ng/ml) after 1 minute of caustic supporting that greater than 99.99% degradation occurs by 1 minute of the alkaline wash. The actual degradation by the end of the alkaline wash which lasts for more than 1 minute is assumed to be significantly higher than 99.99%, and with a SIP included in the cleaning procedure, an even higher % degradation is presumed, e.g., greater than 99.99%.

Without being bound by theory, with excess caustic and constant reaction conditions one can expect additional greater than 99.99% degradation every 1 minute of the alkaline wash and by the end of the alkaline wash of 10 minutes, a degradation of greater than 99.99999999% is expected. Using the sterilization approach of log reduction, where 1 log reduction is 90% microbial kill rate the sterilization time is calculated using 6 log reduction time. We observed more than 99%(2 log) degradation in 1 minutes, if we use similar approach by the end of 5 minutes we can expect 10 log(99.99999999).

Example 6

This example describes a comparison of exemplary SPR based methods using different ligands.

The SPR-based assay described in Example 2 was carried out using one of two different ligands with samples comprising the active form of BiTE molecules which comprises a CD3 binding domain as well as an Fc domain. See FIG. 4A. In a first SPR-based assay, a chip comprising immobilized CD3 (as described in Example 2) was used, while in a second SPR-based assay, a chip comprising Protein A was used.

Figure 4B:
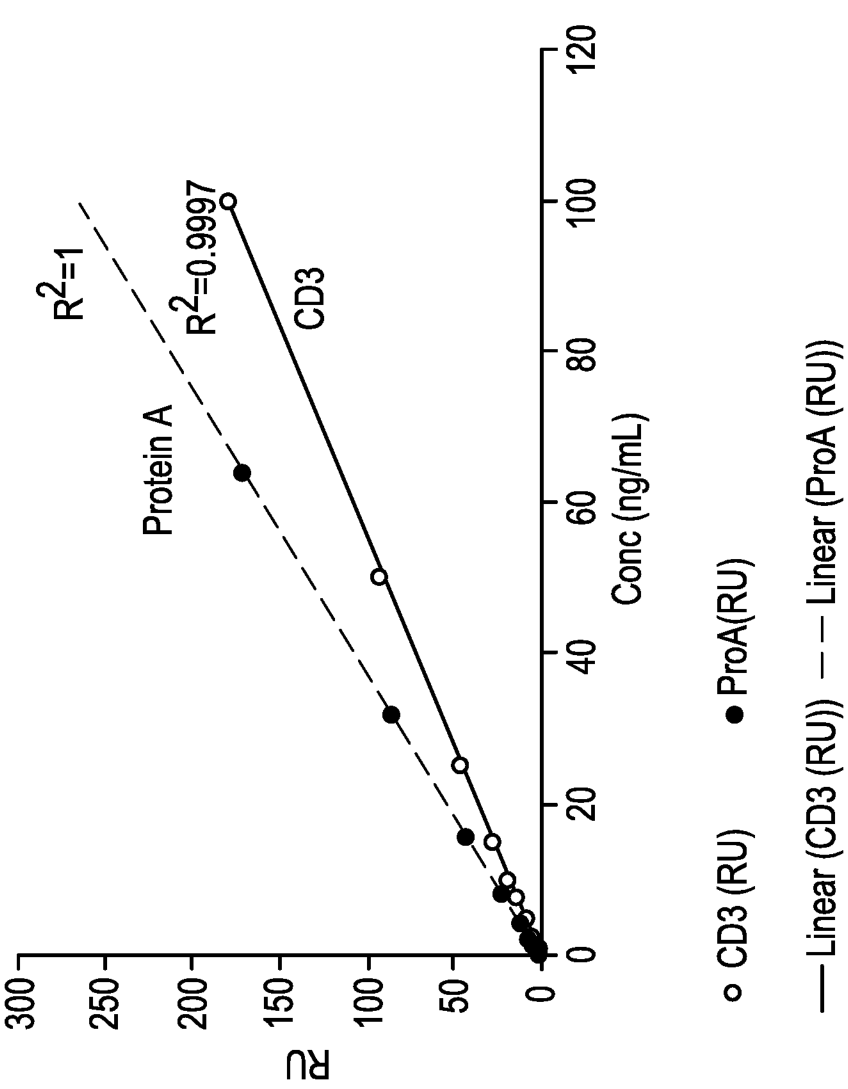
FIG. 4B is a graph of the standard curve when the ligand is CD3 (blue) or when the ligand is protein A (orange). $r^2$ of the linear regression models correlating concentration of the molecule to measured RU (by the SPR instrument) are shown.

Using a series of samples of comprising of known concentrations ranging from 0 ng/mL to 100 ng/ml, a standard curve was made as essentially described in Example 2—one curve using a CD3 as the ligand and one curve using Protein A as the ligand. The results are shown in FIG. 4B. As shown in this figure, Fc binding to the Protein A ligand had a higher response (e.g., steeper slope) compared to binding of the CD3-binding domain to the CD3 ligand. A steeper slope of a regression line demonstrates higher sensitivity.

All references, including publications, patent applications, and patents, cited herein are hereby incorporated by reference to the same extent as if each reference were individually and specifically indicated to be incorporated by reference and were set forth in its entirety herein.

The use of the terms “a” and “an” and “the” and similar referents in the context of describing the disclosure (especially in the context of the following claims) are to be construed to cover both the singular and the plural, unless otherwise indicated herein or clearly contradicted by context. The terms “comprising,” “having,” “including,” and “containing” are to be construed as open-ended terms (i.e., meaning “including, but not limited to,”) unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., “such as”) provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed:

1. A cleaning validation assay for a biotherapeutic manufacturing process, comprising: determining the binding activity of a cleaned sample to a ligand by a surface plasmon resonance (SPR)-based assay, where in the which binds to the biotherapeutic produced by the biotherapeutic manufacturing process wherein the cleaned sample is obtained by carrying out a small-scale cleaning procedure, which simulates a large-scale cleaning procedure, on a sample comprising the biotherapeutic, wherein the cleaning validation assay has a limit of detection (LOD) that is less than 20 ng/mL.

2. The cleaning validation assay of claim 1, wherein the biotherapeutic comprises an Fc domain and/or the ligand is an Fc-binding protein.

3. The cleaning validation assay of claim 2, wherein the biotherapeutic is an antibody.

4. The cleaning validation assay of claim 2, wherein the Fc-binding protein is Protein A, Protein G, or Protein L.

5. The cleaning validation assay of claim 2, wherein the biotherapeutic is a bispecific T-cell engager molecule comprising a CD3-binding domain.

6. The cleaning validation assay of claim 5, wherein the ligand comprises a CD3 epitope that binds to the CD3-binding domain.

7. The cleaning validation assay of claim 1, wherein the acceptable daily exposure (ADE) of the biotherapeutic is 0.1 μg to 1 μg.

8. A method of assessing a cleaning procedure of a biotherapeutic manufacturing process, comprising:

a. carrying out a small-scale cleaning procedure, which simulates a large-scale cleaning procedure, on a sample comprising the biotherapeutic produced by the biotherapeutic manufacturing process, to obtain a cleaned sample, b. determining the binding activity of the cleaned sample to a ligand which binds to the biotherapeutic, wherein the binding activity is determined by a surface plasmon resonance (SPR)-based assay, which correlates the binding activity to a concentration of the biotherapeutic; and c. determining the concentration of the biotherapeutic of the cleaned sample based on the binding activity determined by the SPR-based assay.

9. The method of claim 8, wherein the cleaning procedure comprises at least one degradation step and/or at least one inactivation step purposed for degrading and/or inactivating the biotherapeutic.

10. The method of claim 9, which demonstrates greater than about 99.99% degradation of the biotherapeutic.

11. The method of claim 10, which demonstrates greater than about 99.999% degradation of the biotherapeutic.

12. The method of claim 8, wherein the cleaning procedure comprises an alkaline wash, an acidic wash, a high temperature step, or any combination thereof.

13. The method of claim 8, wherein the cleaned sample is filtered through a filter before determining the binding activity or the method comprises filtering the cleaned sample through a filter to reduce the amount of precipitates or salt crystals in the cleaned sample and/or to reduce the overall volume of the cleaned sample, optionally, wherein the filtering increases a protein concentration of the cleaned sample.

14. The method of claim 13, comprising filtering the cleaned sample through a PES filter and/or a MWCO filter having a MWCO of about 30 kDa to about 50 kDa.

15. The method of claim 8, wherein the ligand is attached to a face of a solid support.

16. The method of claim 8, wherein the binding activity correlates with a concentration of an active form of the biotherapeutic in the solution.

17. The method of claim 16, further comprising comparing the change in the SPR angle to a calibration curve to obtain a concentration of the active form of the biotherapeutic in the solution.

18. The method of claim 8, wherein the biotherapeutic comprises an Fc domain and/or the ligand is an Fc-binding protein.

19. The method of claim 18, wherein the biotherapeutic is an antibody.

20. The method of claim 18, the Fc-binding protein is Protein A, Protein G, or Protein L.

21. The method of claim 8, wherein the biotherapeutic is a bispecific T-cell engager molecule comprising a CD3-binding domain.

22. The method of claim 21, wherein the ligand comprises a CD3 epitope that binds to the CD3-binding domain.

23. The method of claim 8, wherein the limit of detection (LOD) for the active form of the biotherapeutic is less than about 20 ng/mL.

24. The method of claim 8, wherein the LOD for the active form of the biotherapeutic is about 13.0 ng/nL or less.

25. The method of claim 8, wherein the acceptable daily exposure (ADE) of the biotherapeutic is 0.1 μg to 1 μg.

* * * * *